US005683884A

United States Patent [19]
Moore et al.

[11] Patent Number: 5,683,884
[45] Date of Patent: Nov. 4, 1997

[54] METHODS FOR IDENTIFYING MODULATORS OF HUMAN CALCITONIN MEDIATED METABOLISM

[75] Inventors: Emma E. Moore, Seattle; Paul O. Sheppard, Redmond; Rolf E. Kuestner, Bothell, all of Wash.

[73] Assignee: ZymoGenetics, Inc., Seattle, Wash.

[21] Appl. No.: 452,802

[22] Filed: May 30, 1995

Related U.S. Application Data

[60] Division of Ser. No. 100,887, Aug. 2, 1993, abandoned, which is a continuation-in-part of Ser. No. 954,804, Sep. 30, 1992, abandoned.

[51] Int. Cl.$^6$ .......................... G01N 33/53; C12N 15/12; C12N 15/63; C07K 14/72
[52] U.S. Cl. .......................... 435/7.1; 435/7.1; 435/7.21; 435/240.1; 435/240.2; 530/350; 530/399; 530/395; 536/23.1; 536/23.5
[58] Field of Search .................................. 435/7.1, 7.21, 435/240.1, 240.2, 325; 530/350, 399, 395; 536/23.1, 23.5

[56] References Cited

U.S. PATENT DOCUMENTS

5,516,651  5/1996  Goldring et al. .................... 435/69.1

FOREIGN PATENT DOCUMENTS

93/04373  3/1993  WIPO .
93/10149  5/1993  WIPO .
94/21665  9/1994  WIPO .

OTHER PUBLICATIONS

Chovev, M. et al. J. Bone and Mineral Res. 1992 (Aug) vol. 7, Supp. 1 p. 5243.
Lin, H. T. et al. Science (1991) vol. 254:pp. 1022–1024.
Goldring, S.R. et al. Horm. Metab. Res (1993) vol. 25: 477–480.
Chabre, O. et al. Mol Endocrihol (1992) 6: 551–556.
Hendry et al., "Immobilization of Antibodies of Nylon for Use in Enzyme–Linked Immunoassay", *J. Immunol. Meths.* 35:285–296 (1980).
Moseley et al., "The Calcitonin Receptor On T 47D Breast Cancer Cells", *Biochem, J.*, 212:609–616 (1983).
Bouizar et al., "Purification and Characterization of Calcitonin Receptors in Rat Kidney Membranes by Covalent Cross–Linking Techniques", *Eur. J. Biochem*, 155:141–147 (1986).
Sambrook et al., "Synthetic Oligonucleotide Probes", *Molecular Cloning: A Laboratory Manual*, Cold Spring Harbor, NY, pp. 11.2–11.60 (1989).
Libert et al., "Selective Amplification and Cloning of Four New Members of the G Protein–Coupled Receptor Family" *Science* 244:569–572 (May 5, 1989).
Tsai–Morris et al., "Intronic Nature of the Rat Luteinizing Hormone Receptor Gene Defines a Soluble Receptor Subspecies with Hormone Binding Activity", *J. Biol. Chem.* 265:19385–19388 (Nov., 1990).

Raue et al., "The Calcitonin Receptor: Characterization and Processing", *Molecular and Cellular Regulation of Calcium and Phosphate Metabolism*, p. 67–69 (1990).
Lam et al., "A New Type of Synthetic Peptide Library for Identifying Ligand–Binding Activity", *Nature* 354:82–84 (Nov. 9, 1991).
Lin et al., "Expression Cloning of an Adenylate Cyclase–Coupled Calcitonin Receptor", *Science*, 254:1022–1024 (Nov. 15, 1991).
Juppner et al., "A G Protein–Linked Receptor for Parathyroid Hormone and Parathyroid Hormone–Related Peptide", *Science*, 254:1024–1026 (Nov. 15, 1991).
Lin et al., "Expression Cloning and Characterization of a Porcine Renal Calcitonin Receptor", *Trans. Assoc. Am. Physicians* 104:265–272 (1991).
Stern, P. S., "Predicting Antigenic Sites on Proteins," *Tibtech.* 9:163–68 (1991).
Chabre et al., "A Recombinant Calcitonin Receptor Independently Stimulates 3', 5'–Cyclic Adenosine Monophosphate and $Ca^{2+}$Inositol Phosphate Signaling Pathways", *Molecular Endocrinology*, 6(4): 551–556 (1992).
Goldring, "Characterization of a Porcine renal Calcitonin Receptor; Comparison to Other G Protein–Coupled Receptors", *Bone and Mineral*, Abst. 81:42 (1992).
Gorn et al., "Properties of a Calcitonin Receptor Cloned from Human Ovarian Carcinoma Cell", *Bone and Mineral*, Abst., 81:43 (1992).
Muff, et al., "Comparison of a Calcitonin Gene–Related Peptide Receptor in a Human Neuroblastoma Cell Line (SK–N–MC) and a Calcitonin Receptor in a Human Breast Carcinoma Cell Line (T47D)$^a$", *New York Academy of Sciences*, 657:106–116 (1992).
Quirion, et al., "Characterization of $CGRP_1$ and $CGRP_2$ Receptor Subtypes$^{a"}$ *New York Academy of Sciences*, 657:88–105 (1992).
Moore et al., "The Cloned Human Calcitonin Receptor Can Couple to Two Alternative Second Messenger Pathways When Expressed in BHK Cells", *J. Bone Miner. Res.*, Abst., S146:215 (Aug., 1992).
Gorn et al., "Cloning, Characterization, and Expression of a Human Calcitonin Receptor from an Ovarian Carcinoma Cell Line", *J. Clin. Invest.* 90:1726–1735 (Nov., 1992).
Chabre et al., "A Recombinant Calcitonin Receptor Independently Stimulates 3', 5'–Cyclic Adenosine Monophosphate and $Ca^{2+}$/Inositol Phosphate Signaling Pathways" *Mol. Endo.* 6:551–556 (1992).

(List continued on next page.)

Primary Examiner—Stephen Walsh
Assistant Examiner—Daryl A. Basham
Attorney, Agent, or Firm—Townsend and Townsend and Crew

[57] ABSTRACT

Human calcitonin receptors have been cloned, sequenced and expressed by recombinant means. The receptors and antibodies thereto may be used in screening systems to identify agonists and antagonists of human calcitonin receptors, thereby providing means for treating and preventing abnormal bone resorption, as well as in methods of diagnosis.

8 Claims, 3 Drawing Sheets

OTHER PUBLICATIONS

Force et al., "A Cloned Porcine Renal Calcinonin Receptor Couples to Adenylyl Cyclase and Phospholipase C", *Am. J. Physiol.* 262:F1110–F1115 (1992).

Iismaa et al. "G Protein–Coupled Receptors", *Curr. Opin. Cell Biol.* 4:195–202 (1992).

Albrandt et al., "Molecular Cloning of Two Receptors from Rat Brain with High Affinity for Salmon Calcitonin", *FEBS Lett.* 325:225–232 (1993).

Yamin et al., "Analysis of a Unique Murine Brain Calcitonin Receptor (CTR) cDNA and Preliminary Characterization of the Murine CTR Gene; Evidence for the Existence of Functionally Distinct Isoforms of the CTR", *J. Bone. Mineral Res.*, 8 (Supp. 1) p. S129, Abst. 51 (Aug., 1993).

Houssami et al., "Rat Calcitonin Receptor Isoforms Display Functional Heterogeneity", *J. Bone. Mineral Res.*, 8 (Supp. 1) p. S129, Abst. 52 (Aug., 1993).

Gorn et al., "The Cloning of a Human Osteoclast Calcitonin Receptor From A Giant Cell Tumor of Bone (Osteoclastoma)", *J. Bone. Mineral Res.*, 8 (Supp. 1) p. S384, Abst. 1069 (Aug., 1993).

Sexton et al. "Identification of Brain Isoforms of the Rat Calcitonin Receptor", *Mol. Endo.* 7:815–821 (1993).

Nussenzveig et al., "Inhibition of Inositol Phosphate Second Messenger Formation by Intracellular Loop One of a Human Calcitonin Receptor," *J. Biol. Chem.*, 269:28123–28129 (Nov., 1994).

FIG. 1

X
MRFTFTSRCLALFLLLNHPTPILPAFSNQTYPTIEPKPFLYVVGRKKMMDAQYKCYDRMQQLPAYQGE
GPYCNRTWDGWLCWDDTPAGVLSYQFCPDYFPDFDPSEKVTKYCDEKGVWFKHPENNRTWSNYTMCNAFT
                                                         _____
                                                            TMD I
PEKLKNAYVLYYLAIVGHSLSIFTLVISLGIFVFFRSLGCQRVTLHKNMFLTYILNSMIIIHLVEVVPN
_____                      _____
                                                         TMD II
GELVRRDPVSCKILHFFHQYMMACNYFWMLCEGIYLHTLIVVAVFTEKQRLRWYYLLGWGFPLVPTTIHA
                   _____                                 ___
                       TMD III                                     TMD IV
ITRAVYFNDNCWLSVETHLLYIIHGPVMAALVVNFFFLLNIVRVLVTKMRETHEAESHMYLKAVKATMIL
_____           _____
                                 TMD V
VPLLGIQFVVFPWRPSNKMLGKIYDYVMHSLIHFQGFFVATIYCFCNNEVQTTVKRQWAQFKIQWNQRWG
_____                    _____
  TMD VI                            TMD VII
RRPSNRSARAAAAAEAAGDIPIYICHQELRNEPANNQGEESAEIIPLNIIEQESSA.         X

METHODS FOR IDENTIFYING MODULATORS OF HUMAN CALCITONIN MEDIATED METABOLISM

This application is a divisional of Ser. No. 08/100,887, filed Aug. 2, 1993, now abandoned, which is a continuation-in-part of Ser. No. 07/954,804, filed Sep. 30, 1992 (now abandoned), which are incorporated herein by reference.

BACKGROUND OF THE INVENTION

Bone is a dynamic tissue, and homeostasis requires a balance between the formation of new bone and the resorption of previously formed bone. Calcitonin, a peptide hormone secreted by the thyroid and thymus, plays an important role in maintaining bone homeostasis. Calcitonin binds to osteoclasts, cells in the bone tissue which mediate bone resorption. Calcitonin immobilizes osteoclasts, thus inhibiting bone resorption with a resultant decrease in the amount of calcium released by bone into the serum. The inhibition of bone resorption has been exploited by using calcitonin as a treatment for osteoporosis.

The calcitonin receptor is believed to be a member of the G-protein coupled receptor family. It has been demonstrated that activation of the receptor results in stimulation of two independent intracellular pathways, the cyclic AMP and inositol triphosphate pathways (Chabre et al., Molec. Endocrin. 6(4): 551-556, 1992). The cloning of the parathyroid hormone, porcine calcitonin, secretin and glucagon receptors has established the possibility that a new family of G protein-coupled receptors exists. These receptors show little homology to the previously known G protein coupled receptors that included the beta adrenergic receptor, the serotonin receptor and the glutamate receptors.

At the present time, salmon calcitonin is preferred over human calcitonin for treatment of osteoporosis. The worldwide market for salmon calcitonin exceeds $500 million annually. Salmon calcitonin has been shown to be considerably more effective in arresting bone resorption than human forms of calcitonin. There are several hypotheses for why salmon calcitonin is more potent than human calcitonin in treatment for osteoporosis. These hypotheses include: 1) salmon calcitonin is more resistant to degradation, 2) salmon calcitonin has a lower metabolic clearance rate (MCR) and 3) salmon calcitonin may have a slightly different conformation, resulting in a higher affinity for bone receptor sites.

Despite the advantages associated with the use of salmon calcitonin for treatment of osteoporosis in humans, there are also disadvantages. The average cost can exceed $200 per month, and treatment involves prophylactic administration for 5 or more years. Another problem is that, in the United States, calcitonin must be administered by injection. In addition, some patients develop antibodies to non-human calcitonin. Therefore, new analogs of salmon or human calcitonin that are potent inhibitors of bone resorption, less expensive, more convenient to administer and non-immunogenic are needed.

The discovery and testing of possible compounds for use as calcitonin analogs require high through-put screening systems. Such a system would preferably use a cellular target, such as a cultured cell line containing high levels of the appropriate calcitonin receptor, to identify and measure responses to putative analogs. Quite surprisingly, the present invention provides human calcitonin receptors for use in screening systems for identifying calcitonin analogs, and fulfills other related needs.

SUMMARY OF THE INVENTION

The present invention provides isolated and substantially pure preparations of human calcitonin receptor, recombinant human calcitonin receptor, and polypeptide fragments thereof. Within certain embodiments the receptors are coupled to a G protein in vertebrate cells, bind calcitonin and thereby activate adenylate cyclase, and are capable of stimulating inositol phosphate metabolism. Within other embodiments, the receptors are in a truncated form. Having provided such recombinant receptors in isolated and purified form, the invention also provides monoclonal antibodies to the receptors, the calcitonin binding domains, and other fragments.

In another aspect the invention provides the ability to produce human calcitonin receptors and polypeptides or fragments thereof by recombinant means, preferably in cultured eukaryotic cells. The expressed receptors or fragments may or may not have the biological activity of native receptor, and may or may not be coupled to a G protein in the cell used for expression. Accordingly, isolated and purified polynucleotides are described which code for human calcitonin receptors and fragments thereof, where the polynucleotides may be in the form of DNA, such as cDNA, or RNA. Based on these sequences probes may be used to hybridize and identify the human calcitonin receptor gene. The probes may be full length cDNA or as small as from 14 to 25 nucleotide, more often though from about 40 to about 50 or more nucleotides.

In related embodiments the invention concerns DNA constructs which comprise a transcriptional promoter, a DNA sequence which encodes the human calcitonin receptor or fragment, and a transcriptional terminator, each operably linked for expression of the receptor. For expression the construct may also contain at least one signal sequence. The constructs are used to transform or transfect host cells, preferably mammalian cells and more preferably those which do not express substantial amounts of endogenous calcitonin receptor. When bound by an appropriate ligand such as calcitonin, the receptor may activate adenylate cyclase in the host cell via coupling to G protein. Further, for large scale production the expressed receptor may also be isolated from the cells by, for example, affinity purification.

Cells which express human calcitonin receptor can be used to identify compounds which can alter the calcitonin receptor-mediated metabolism of a eukaryotic cell. Compounds may be screened for binding to the receptor, and/or for effecting a change in receptor-mediated metabolism in the host cell. Agonists and/or antagonists of the receptors may also be screened in cell-free systems using purified receptors or binding fragments thereof for the effect on ligand-receptor interaction, or using reconstituted systems such as micelles, which also provide the ability to assess metabolic changes. The compounds identified according to the invention can serve as lead compounds for subsequent development or screening of drugs useful in the treatment and prevention of bone resorption related disorders, such as osteoporosis, Paget's disease, and the like.

BRIEF DESCRIPTION OF THE DRAWINGS

FIG. 1 illustrates the amino acid sequence of a human calcitonin receptor (Seq. ID No. 1), with putative transmembrane domains overlined;

DESCRIPTION OF THE SPECIFIC EMBODIMENTS

Figure 2:
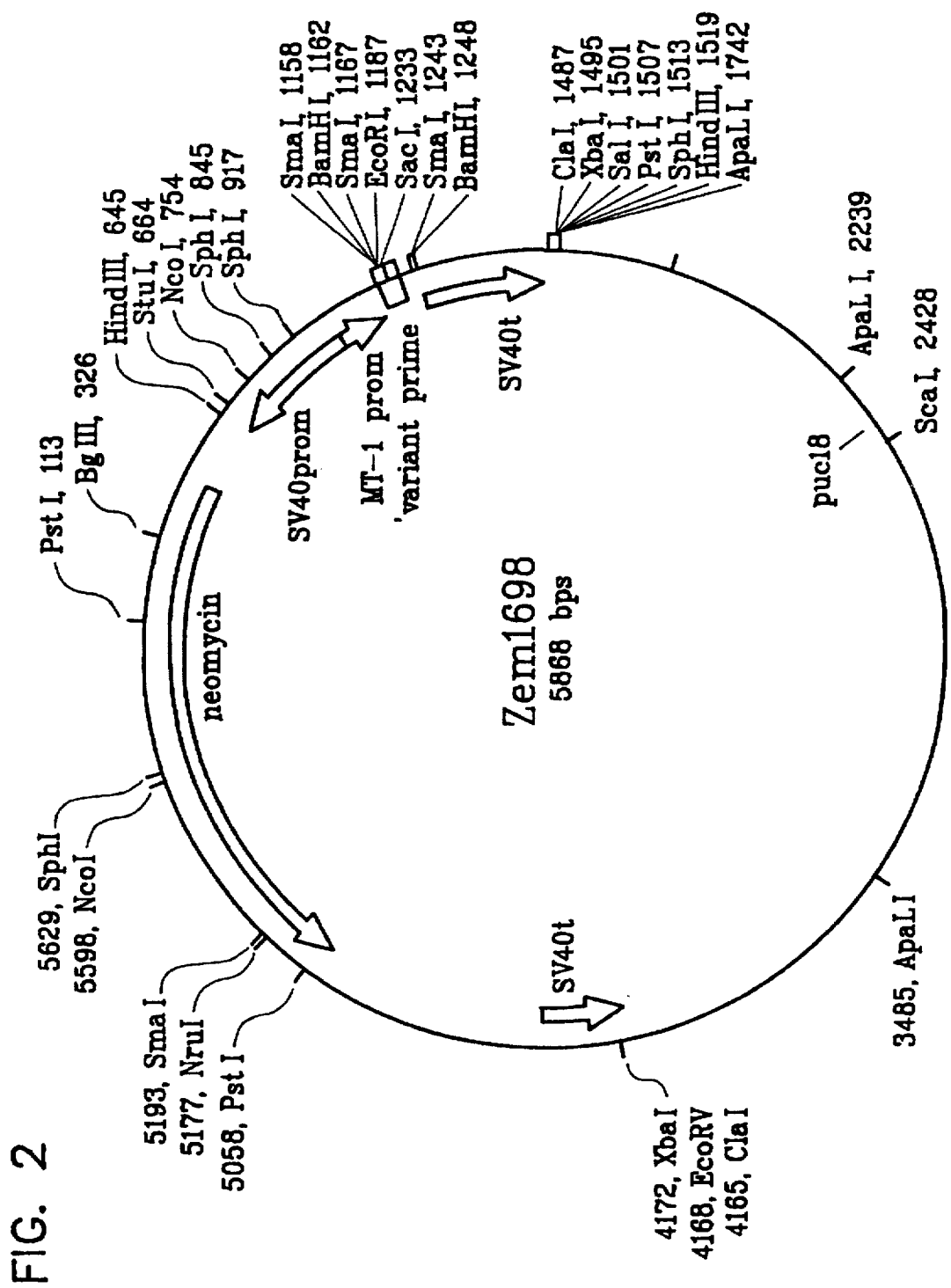
FIG. 2 is the vector ZEM1698.

The present invention presents the means to identify agonists and antagonists of the human calcitonin receptor-ligand interaction by providing isolated human calcitonin receptor molecules, recombinant human calcitonin receptor and the isolated polynucleotide sequences which encode the receptors. The term "human calcitonin receptor" refers to any protein which shares significant structural and functional homology with the calcitonin receptor set forth in the amino acid sequence of FIG. 1. Such a receptor may result when regions of a recombinantly prepared human calcitonin receptor are deleted or replaced in such a manner as to yield a protein having a similar function. Substantially homologous sequences, allelic variations, and natural mutants; induced point, deletion, and insertion mutants and alternatively expressed variants are also included. As used herein, substantially homologous means sequences which are at least 80%, preferably at least 90%, and more preferably 95% or more identical to sequences of the human cDNA sequences shown in Seq. ID No. 1. The essential functional aspects of the calcitonin receptor are that when inserted into a plasma membrane it is capable of binding human calcitonin, and that it is capable of initiating a cellular response in response to that binding.

Variants of the calcitonin receptor may be truncated, resulting in a receptor that binds human calcitonin but does not initiate a cellular response. The essential functional requirement of such a receptor variant is that it contain a ligand-binding domain capable of binding calcitonin.

Variants of the calcitonin receptor include variants having insertions located in a DNA sequence immediately following the first transmembrane region. While not wanting to bound by theory, certain of these variants may function as soluble forms of the calcitonin receptor. Soluble forms of other predominately transmembrane receptors have been found previously. For example, the luteinizing hormone receptor, a member of the seven-transmembrane G protein-coupled receptor family, has been shown to bind ligand in a truncated form that comprises only the extracellular domain of the receptor (Tsai-Morris et al. *J. Biol. Chem.* 265(32): 19385–19388, 1990). It has been postulated that the truncated form of a receptor could bind ligand and affect the concentration of hormone available for interaction with target cells expressing the membrane-bound receptor.

Other receptor variants having insertions after the first transmembrane region are believed to remain anchored in the membrane but affect the signal transduction properties within the cell. In the case where the insertion results in a truncated variant of the receptor but the receptor remains membrane-bound, the intracellular signalling property of the receptor-ligand complex is essentially eliminated. A receptor without signal transducing capacity would serve a function similar to a soluble receptor, that is to alter the concentration of hormone that binds to signal transducing receptors without initiating a response in the intracellular signalling pathway and thereby limit the effect of ligand on the cell.

In the case where the variant receptor does not result in a truncated receptor, insertions may alter the cytoplasmic loop, the region correlated to interaction of the G protein-coupled receptor and G protein (Iismaa et al., *Curr. Opinion Cell Biol.* 4:195:202, 1992). Changes in the coupling of the G protein to the receptor affect the second messenger pathway by altering intracellular levels of cAMP, inositol triphosphate or calcium and ultimately can affect bone homeostasis. Specific tissues have been found to express receptor subtypes with different signal transduction properties. For example, metabotropic glutamate receptors include at least five different subtypes of receptors having varying effects on second messengers levels (Schoepp et al., *TIPS* 14:13–20, 1993). Metabotropic glutamate receptor subtypes have been isolated from a variety of different tissues including heart, lacrimal glands, intestine, trachea and hippocampus (Bonner, *TIPS*, Suppl.11–15, 1989). Another instance where variant receptor subtypes may be preferentially expressed is in response to changes in the extracellular environment. The expression of the variant receptors result in changes in the cell's response to ligand. For example, many patients given long term treatment with calcitonin become resistant to the effects of the drug. In approximately 50% of these cases resistance is not accompanied with antibody formation (*The Calcitonins: Physiology and Pharmacology*, Azria ed. Karger, Basel, Su., 1989) and while such resistance is not clearly understood, it has been postulated that the long term exposure to increased levels of calcitonin may induce the expression of an alternative receptor subtype and thus change the cell's responsiveness to calcitonin. The calcitonin receptors and variants of the present invention provide valuable tools for studying cellular responses to calcitonin under a variety of conditions and for identifying compounds that regulate calcitonin-responsive cellular pathways.

By human calcitonin receptor "ligand" is meant a molecule capable of being bound by the ligand-binding domain of human calcitonin receptor, a human calcitonin receptor analog, or chimeric human calcitonin receptor as generally described in U.S. Pat. No. 4,859,609, incorporated by reference herein. The ligand may be chemically synthesized or may occur in nature, such as human or salmon calcitonin. Ligands may be grouped into agonists and antagonists. Agonists are those molecules whose binding to a receptor induces the response pathway within a cell. Antagonists are those molecules whose binding to a receptor blocks the induction of a response pathway within a cell.

"Isolated" human calcitonin receptor is meant to refer to human calcitonin receptor which is in other than its native environment such as an osteoclast, renal cell, lymphocyte, etc., including, for example, substantially pure human calcitonin receptor as defined hereinbelow. More generally, isolated is meant to include human calcitonin receptor as a heterologous component of a cell or other system. For example, human calcitonin receptor may be expressed by a cell transfected with a DNA construct which encodes human calcitonin receptor, separated from the cell and added to micelles which contain other selected receptors. In another example described below, human calcitonin receptor is expressed by a cell which has been co-transfected with a gene encoding luciferase. Thus, in this context, the environment of isolated human calcitonin receptor is not as it occurs in its native state, particularly when it is present in a system as an exogenous component.

The invention provides cloned human calcitonin receptor coding sequences which are capable of expressing the human calcitonin receptor protein. Complementary DNA encoding human calcitonin receptor may be obtained by constructing a cDNA library from mRNA obtained from, for example, osteoclasts, breast carcinoma cells which are known to express the receptor, such as T-47D described hereinbelow, etc. The library may be screened with a labeled complementary oligonucleotide probe. Alternatively, the library may be screened by transcribing the library and injecting the resulting mRNA into appropriate eucaryotic cells and detecting, by functional assays, those transfected cells which express the human calcitonin receptor.

The present invention relates to successfully isolating cDNA encoding a human calcitonin receptor. With the human calcitonin receptor and cDNA clones thereof provided herein, nucleotide and amino acid sequences may be determined by conventional means, such as by dideoxy sequencing. See generally, Sambrook et al., *Molecular Cloning, A Laboratory Manual*, 2d ed., Cold Spring Harbor Laboratory Press, Cold Spring Harbor, N.Y., 1989, incorporated by reference herein. Based on the sequences herein provided, genomic or cDNA sequences encoding human calcitonin receptor may be obtained from libraries prepared from human cell sources according to well known procedures. For instance, using oligonucleotide probes from human calcitonin receptor, such as whole length cDNA or shorter probes of at least about fourteen nucleotides to twenty-five or more nucleotides in length; often as many as 40 to 50 nucleotides, DNA sequences encoding other human calcitonin receptor subtypes may be obtained. If partial clones are obtained, it is necessary to join them in proper reading frame to produce a full length clone, using such techniques as endonuclease cleavage, ligation and loopout mutagenesis.

A DNA sequence encoding human calcitonin receptor is inserted into a suitable expression vector, which in turn is used to transfect eukaryotic cells. Expression vectors for use in carrying out the present invention will comprise a promoter capable of directing the transcription of a cloned DNA and a transcriptional terminator.

To direct proteins of the present invention for transport to the plasma membrane, at least one signal sequence is operably linked to the DNA sequence of interest. The signal sequence may be derived from the human calcitonin receptor coding sequence, from other signal sequences described in the art, or synthesized de novo.

Host cells for use in practicing the present invention include mammalian, avian, plant, insect and fungal cells, but preferably mammalian cells. Fungal cells, including species of yeast (e.g., Saccharomyces spp., particularly *S. cerevisiae*, Schizosaccharomyces spp.) or filamentous fungi (e.g., Aspergillus spp., Neurospora spp.) may be used as host cells within the present invention. Suitable yeast vectors for use in the present invention include YRp7 (Struhl et al., *Proc. Natl. Acad. Sci. USA* 76:1035–1039, 1978), YEp13 (Broach et al., *Gene* 8:121–133, 1979), POT vectors (Kawasaki et al, U.S. Pat. No. 4,931,373, which is incorporated by reference herein), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8:17, 1979), HIS3 (Struhl et al., ibid.) or POT1 (Kawasaki et al., ibid.). Another suitable selectable marker is the CAT gene, which confers chloramphenicol resistance to yeast cells.

Additional vectors, promoters and terminators which can be used in expressing the receptors of the invention in yeast are known in the art and are reviewed by, for example, Emr (*Meth. Enzymol.* 185:231–279, 1990), incorporated herein by reference. The receptors of the invention may be expressed in Aspergillus spp. (McKnight and Upshall, described in U.S. Pat. No. 4,935,349, which is incorporated herein by reference). Useful promoters include those derived from *Aspergillus nidulans* glycolytic genes, such as the ADH3 promoter (McKnight et al., *EMBO J.* 4:2093–2099, 1985) and the tpiA promoter. An example of a suitable terminator is the ADH3 terminator (McKnight et al., ibid.). Techniques for transforming fungi are well known in the literature, and have been described, for instance by Beggs (ibid.), Hinnen et al. (*Proc. Natl. Acad, Sci. USA* 75:1929–1933, 1978), Yelton et al. (*Proc. Natl. Acad. Sci. USA* 81:1740–1747, 1984), and Russell (*Nature* 301:167–169, 1983) each of which are incorporated herein by reference.

A variety of higher eukaryotic cells may serve as host cells for expression of the human calcitonin receptor. Cultured mammalian cells, such as BHK, N1E-115 (Liles et al., *J. Biol. Chem.* 261:5307–5313, 1986), PC 12 and COS-1 (ATCC CRL 1650) are preferred. Preferred BHK cell lines are the tk⁻ts13 BHK cell line (Waechter and Baserga, *Proc. Natl. Acad. Sci. USA* 79:1106–1110, 1982) and the BHK 570 cell line (deposited with the American Type Culture Collection, 12301 Parklawn Dr., Rockville, Md. under accession number CRL 10314). A tk⁻BHK cell line is available as ATCC CRL 1632. It is preferred to use host cells that do not have endogenous calcitonin receptor.

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-1 promoter (Palmiter et al., U.S. Pat. No. 4,579,821), a mouse $V_k$ promoter (Bergman et al., *Proc. Natl. Acad. Sci. USA* 81:7041–7045, 1983; Grant et al., *Nuc. Acids Res.* 15:5496, 1987) and a mouse $V_H$ promoter (Loh et al., *Cell* 33:85–93, 1983). A particularly preferred promoter is the major late promoter from Adenovirus 2 (Kaufman and Sharp, *Mol. Cell. Biol.* 2:1304–13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes.

Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse enhancer (Gillies, *Cell* 33:717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981;

Graham and Van der Eb, *Virology* 52:456, 1973.) Other techniques for introducing cloned DNA sequences into mammalian cells, such as electroporation (Neumann et al., *EMBO J.* 1:841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. Selectable markers are reviewed by Thilly (*Mammalian Cell Technology*, Butterworth Publishers, Stoneham, Mass., which is incorporated herein by reference). The choice of selectable markers is well within the level of ordinary skill in art Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods suitable for introducing expression vectors encoding recombinant human calcitonin receptor into plant, arian and insect cells are known in the art. The use of baculoviruses, for example, as vectors for expressing heterologous DNA sequences in insect cells has been reviewed by Atkinson et al. (*Pestic. Sci.* 28: 215–224, 1990). The use of *Agrobacterium rhizogenes* as vectors for expressing genes in plant cells has been reviewed by Sinkar et al. (*J. Biosci. (Banglaore)* 11:47–58, 1987).

Host cells containing DNA constructs of the present invention are then cultured to produce recombinant human calcitonin receptor. The cells are cultured according to accepted methods in a culture medium containing nutrients required for growth of mammalian or other host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

The human calcitonin receptor produced according to the present invention may be purified from the recombinant expression systems or other sources using purification protocols that employ techniques generally available to those skilled in the art. The most convenient sources for obtaining large quantities of human calcitonin receptor are cells which express the recombinant receptor.

Purification may be achieved by conventional chemical purification means, such as liquid chromatography, lectin affinity chromatography, gradient centrifugation, and gel electrophoresis, among others. Methods of protein purification are known in the art (see generally, Scopes, R., *Protein Purification*, Springer-Verlag, N.Y. (1982), which is incorporated herein by reference) and may be applied to the purification of the human calcitonin receptor and particularly the recombinantly produced human calcitonin receptor described herein. In a preferred embodiment immunoaffinity chromatography is employed using antibodies directed against human calcitonin receptor. In another method of purification, the recombinant gene encoding human calcitonin receptor or portions thereof can be modified at the amino terminus, just behind a signal peptide, with a sequence coding for a small hydrophilic peptide, such as described in U.S. Pat. Nos. 4,703,004 and 4,782,137, incorporated herein by reference. Specific antibodies for the peptide facilitate rapid purification of human calcitonin receptor, and the short peptide can then be removed with enterokinase.

Thus, as discussed above, the present invention provides recombinant human calcitonin receptor isolated from its natural cellular environment, substantially free of other G protein coupled calcitonin receptors. Purified human calcitonin receptor is also provided. Substantially pure human calcitonin receptor of at least about 50% is preferred, at least about 70–80% more preferred, and 95–99% or more homogeneity most preferred, particularly for pharmaceutical uses. Once purified, partially or to homogeneity, as desired, the recombinant human calcitonin receptor may then be used to screen for agonist compounds, generate monoclonal antibodies, in assay Procedures, etc.

In another aspect, the invention concerns polypeptides and fragments of recombinant human calcitonin receptor, including naturally occurring truncated receptor variants. Polypeptides and fragments of human calcitonin receptor may be isolated from recombinant expression systems or may be synthesized from the sequences provided herein by the solid phase method of Merrifield, *Fed. Proc.* 21:412 (1962), Merrifield, *J. Am. Chem. Soc.* 85:2149 (1963), or Barany and Merrifield, in *The Peptides*, vol. 2, pp. 1–284 (1979) Academic Press, NY, each of which are incorporated herein by reference, or by use of an automated peptide synthesizer. By "polypeptides" is meant a sequence of at least about 6 amino acids, typically 20–30 or more, up to 100–200 amino acids or more, including entire proteins. For example, the portion(s) of human calcitonin receptor protein which binds ligand may be identified by a variety of methods, such as by expressing various receptor polypeptide fragments by recombinant techniques or by treating purified recombinant receptor with a protease or a chemical agent to fragment it and determine which fragment is able to bind to labeled calcitonin in a ligand blot. Evidence indicates that a ligand binding domain is contained within about 150 N-terminal residues of the receptor. Polypeptides may then be synthesized and used as antigen, to inhibit ligand-human calcitonin receptor interaction, etc.

In another aspect, the invention provides means for regulating the human calcitonin receptor-ligand interaction, and thus treating, therapeutically and/or prophylactically, a disorder which can be linked directly or indirectly to human calcitonin receptor or to its natural ligand, calcitonin. By virtue of having the receptor of the invention, agonists or antagonists may be identified which stimulate, mimic or inhibit the interaction of human calcitonin with its receptor. With either agonists or antagonists the metabolism and reactivity of cells which express the receptor are controlled, thereby providing a means to abate or in some instances prevent the disease of interest, e.g., osteoporosis.

Thus, the invention provides screening procedures for identifying agonists or antagonists of events mediated by the calcitonin-human calcitonin receptor interaction. Such screening assays may employ a wide variety of formats, depending to some extent on which aspect of the ligand/receptor/G protein interaction is targeted. For example, such assays may be designed to identify compounds which bind to the receptor and thereby block or inhibit interaction of the receptor with the ligand. More preferably, other assays can be designed to identify compounds which can substitute for ligand and therefore stimulate human calcitonin receptor-mediated intracellular pathways. Yet other assays can be used to identify compounds which inhibit or facilitate the association of human calcitonin receptor to G protein and thereby mediate the cellular response to human calcitonin receptor ligand.

In one functional screening assay, human calcitonin receptor expressed within mammalian cells is functionally coupled to inositol metabolism. In this assay, compounds are screened for their relative affinity as receptor agonists orantagonists by comparing the relative receptor occupancy to the extent of ligand-induced stimulation or inhibition of second messenger metabolism. For example, activation of phospholipase C leads to increased inositol monophosphate metabolism. Means for measuring inositol monophosphate metabolism are generally described in Subers and Nathanson, *J. Mol. Cell, Cardiol.* 20:131–140 (1988), incorporated herein by reference.

The screening Procedure can be used to identify reagents such as calcitonin analogues or lead compounds for use in further drug screening which specifically bind to the receptor and substantially affect (stimulate or inhibit) the receptor's ability to stimulate G-protein mediated activation of adenyl cyclase, for example.

The membrane-bound calcitonin receptor of the present invention also appears to function as a calcium receptor. Baby hamster kidney cells expressing recombinant calcitonin receptor were found to respond to millimolar increases in extracellular calcium via a rapid and sustained elevation in $[Ca^{2+}]_i$, whereas three calcitonin receptor-negative baby hamster kidney cell lines, two of which express recombinant receptors related to the calcitonin receptor, showed no sensitivity to changes in extracellular calcium. The calcitonin receptor of the present invention is therefore a useful tool for identifying compounds that can modulate, mimic or inhibit the effects of extracellular calcium on cellular metabolism. Experimental evidence indicates that extracellular calcium regulates parathyroid hormone-secreting chief cells and calcitonin-secreting thyroid C-cells, which secrete their respect hormones in response to serum calcium changes (Zaidi, *Biosci. Rep.* 10:493–506, 1990). Evidence also indicates that osteoclasts express a cell-surface receptor that senses millimolar increases in extracellular calcium and inhibits bone resorption via an increase in osteoclast $[Ca^{2+}]_i$ concentrations (Zaidi, ibid; Alam et al., *Biosci. Rep.* 12:369–380, 1992; MacIntyre et al. in *Handbook of Experimental Pharmacology*, Baker, ed., 83:411–439, Springer-Verlag, Berlin, 1988; Malgaroli et al., *J. Biol. Chem.* 264:14342–14347, 1989; Zaidi et al., *Biochem. Biophys. Res. Commun.* 164:807, 1990).

Truncated calcitonin receptor variants that function as soluble receptors can be used in a variety of screening assays. For example, a soluble receptor may used to screen peptide or non-peptide libraries that have been affixed to a solid support, such as latex, polystyrene beads (Interfacial Dynamics Corp. Portland, Oreg.), magnetic particles (Advanced Magnetics, Cambridge, Mass.) and nylon balls (Hendry et al., *J. Immunological Meth.*, 35:285–296, 1980). For example, it is possible to screen large peptide libraries that are synthesized by distributing a pool of resin beads into separate reaction vessels each with a single amino acid, coupling the amino acids to the beads and then repooling the beads. The cycle is repeated multiple times to extend the peptide chain. Each bead contains a single peptide chain species. An acceptor molecule (e.g. soluble receptor) is coupled to a reporter enzyme (e.g. fluorescein) and allowed to react with peptide chain-coupled beads. The beads that bind receptor are identified by the activation of the reporter enzyme and separated from the pool. The receptor is removed by washing in an appropriate solvent, the peptide chain-coupled bead is placed in a microsequencer, and the amino acid sequence is analyzed (Lam et al., *Nature* 354:82–84, 1991). In another approach, the soluble form of a receptor may be attached to the solid support and ligand passed over the receptor to screen for compounds that bind and form a complex. This screening method is analogous to immobilizing antigens or antibodies to a solid support such as a nylon bead for use in solid-phase enzyme-linked immunoassays (Hendry et al., ibid, 1980). Such methods are well known in the art. The truncated calcitonin receptor variants may also be used to screen peptide libraries as described in WO 91/19818 and WO 91/05058, incorporated herein by reference.

Monoclonal antibodies which bind human calcitonin receptor are also provided by the present invention. The production of non-human monoclonal antibodies, e.g., murine, is well known (see, e.g., Harlow et al., *Antibodies A Laboratory Manual*, Cold Spring Harbor Press, pp. 139–240, 1989, incorporated herein by reference) and may be accomplished by, for example, immunizing the animal with the purified recombinant human calcitonin receptor molecule or a preparation containing a desired portion of the receptor molecule, such as the domain or domains which contribute to ligand binding or to G protein and adenylate cyclase activation. As it may be difficult to generate human monoclonal antibodies to a human receptor or binding domain polypeptide, it may be desirable to transfer antigen binding regions of non-human monoclonal antibodies, e.g. the $F(ab')_2$ or hypervariable regions or murine monoclonal antibodies, to human constant regions (Fc) or framework regions by recombinant DNA techniques to produce substantially human molecules. Such methods are generally known and are described in, e.g., U.S. Pat. Nos. 4,816,397 and 4,946,778, and EP publications 173,494 and 239,400, which are incorporated herein by reference. Alternatively, one may isolate DNA sequences which code for a human monoclonal antibody or portions thereof that specifically bind to the human receptor protein by screening a DNA library from human B cells according to the general protocol outlined in WO 90/14430, incorporated herein by reference, and then cloning and amplifying the sequences which encode the antibody (or binding fragment) of the desired specificity.

In other embodiments, the invention provides screening assays conducted in vitro with cells which express the receptor. For example, the DNA which encodes the receptor or selected portions thereof may be transfected into an established cell line, e.g., a mammalian cell line such as BHK or CHO, using Procedures described herein. The receptor is then expressed by the cultured cells, and selected agents are screened for the desired effect on the cell, separately or in conjunction with an appropriate ligand such as calcitonin.

In yet another aspect, the screening assays provided by the invention relate to transgenic mammals whose germ cells and somatic cells contain a nucleotide sequence encoding human calcitonin receptor protein or a selected portion of the receptor which, e.g., binds ligand, GTP binding protein, or the like. There are several means by which a sequence encoding, for example, the human calcitonin receptor may be introduced into a non-human mammalian embryo, some of which are described in, e.g., U.S. Pat. No. 4,736,866, Jaenisch, *Science* 240-1468–1474 (1988) and Westphal et al., *Annu. Rev. Cell Biol.* 5:181–196 (1989), which are incorporated herein by reference. The animal's cells then express the receptor and thus may be used as a convenient model for testing or screening selected agonists or antagonists.

In another aspect the invention concerns diagnostic methods and compositions. By means of having nucleotide sequences encoding the human calcitonin receptor, the recombinant receptor protein and monoclonal antibodies thereto, a variety of diagnostic assays are provided. For example, with monoclonal antibodies to human calcitonin receptor, the presence and/or concentration of receptor in selected cells or tissues of an individual or culture of interest may be determined. These assays can be used in the diagnosis and/or treatment of diseases such as, for example, osteoporosis, Paget's disease, and other bone resorption disorders, for example. Numerous types of immunoassays and oligonucleotide probe assays are available and are known to those skilled in the art.

The human calcitonin receptor DNA or RNA may be directly detected in cells with a labeled human calcitonin receptor oligonucleotide probe in a hybridization Procedure similar to the Southern or dot blot. Also, the polymerase chain reaction (Saiki et al., *Science* 239:487, 1988, and U.S. Pat. No. 4,683,195 and 4,683,202, incorporated herein by reference) may be used to amplify DNA sequences, which are subsequently detected by their characteristic size on agarose gels, Southern blots of these gels using human calcitonin receptor DNA or a oligonucleotide probe, or a dot blot using similar probes. The probes may comprise from about 14 nucleotides to about 25 or more nucleotides, preferably, 40 to 60 nucleotides, and in some instances a substantial portion or even the entire cDNA of human calcitonin receptor may be used. The probes are labeled, directly or indirectly, with a with a detectable signal, such as an enzyme, biotin, a radionuclide, fluorophore, chemiluminescer, paramagnetic particle, etc.

The following examples are offered by way of illustration, not by limitation.

EXAMPLE I

Cloning Human Calcitonin Receptor

This Example describes methods for cloning human calcitonin receptor cDNAs.

I. Synthesis of cDNA and Preparation of cDNA Library

T-47D breast carcinoma cells (HBL 133) were obtained from the American Tissue Culture Collection (ATCC) and cultured to confluency in 150 mm petri dishes containing RPMI medium (RPMI 1640 (Sigma, St. Louis, Mo.); 0.29 mg/ml L- glutamine (Hazelton, Lenexa, Kans.); 1 mM sodium pyruvate (Irvine, Santa Ana, Calif.); 0.6 µl/ml insulin (GIBCO-BRL, Gaithersburg, Md.) and 1 µM hydrocortisone (Sigma). The cells were removed by scraping from the petri dishes and total RNA was prepared from the cells using guanidine isothiocyanate (Chirgwin et al. *Biochemistry* 18:52–94, 1979) and CsCl centrifugation. Poly (A)+ RNA was isolated using oligo d(T) cellulose chromatography (Aviv and Leder, *Proc. Natl. Acid. Sci. USA* 69:1408–1412, 1972). The RNA was twice selected for poly (A)+ RNA.

First strand cDNA was synthesized from the poly (A)+ RNA described above. A reaction was prepared with the following reagents: 5.0 µl of 2.0 µg/µl poly (A)+ RNA, 7.0 µl of water treated with diethyl pyrocarbonate (DEPC), 2.0 µl 10 mM Tris and 1 mM EDTA (TE) pH 7.4, and 2.0 µl of 1.0 µg/µl oligonucleotide ZC2938 (Sequence ID. No. 15) to act as a primer. The reaction mixture was heated to 65° C. for 3 minutes and cooled on ice. After cooling the reaction mixture was divided into separate tubes designated A and B. The following reagents were added to both the A and B mixtures: 4.0 µl of 5× AT buffer (GIBCO-BRL, Gaithersburg, Md.), 1.0 µl of 200 mM dithiothreitol, 1.0 µl of a deoxynucleotide triphosphate solution containing 10 mM of each dATP, dGTP, dTTP and 5- methyl-dCTP (Pharmacia LKB Biotechnology, Piscataway, N.J.). Reaction mixture A had 1.0 µl of the radiolabeled deoxynucleotide triphosphate α-dATP (10 µCi/µl) added. To the reaction mixture B 1.0 µl of DEPC-treated water was added. Five microliters of 200 µ/µl Superscript® reverse transcriptase (GIBCO-BRL, Gaithersburg, Md.) was added to both reaction mixtures A and B, and both were incubated at 45° C. for 30 minutes. The reactions were terminated by adding 80.0 µl of TE pH 7.4.

Two microliters were removed from reaction mixture A to quantitate the yield using a TCA precipitation. An additional 2.0 µl were set aside for alkaline gel analysis. The remaining reaction mixtures A and B were precipitated by adding 2.0 µg oyster glycogen, 30.0 µl 8M $NH_4Ac_2$ and 300.0 µl 100% ethanol. After pelleting the reactions were resuspended in 50.0 µl sterile distilled water.

Second strand synthesis was performed on the RNA-DNA hybrid from the first strand synthesis reaction under conditions that promoted first strand priming of second strand synthesis resulting in DNA hairpin formation. A 100.0 µl reaction mixture was prepared by adding the following reagents to the 50 µg of first strand cDNA: 20.0 µl of 5× polymerase I buffer (100 mM Tris, pH 7.4, 500 mM KCl, 25 mM $MgCl_2$, 50 mM $(NH_4)_2SO_4$), 4.0 µl 100 mM dithiothreitol, 1.0 µl of a solution containing 10 mM of each deoxynucleotide triphosphate, 3.0 µl of 5 mM β-NAD, 0.6 µl of 7 µ/µl *E. coli* DNA ligase (NEB, Beverly, Mass.), 3.1 µl of 8 µ/µl *E. coli* DNA polymerase (Amersham, Arlington Heights, Ill.), 1 µl of 2.0 µu/µl RNase H (GIBCO-BRL, Gaithersburg, Md.). Reaction mixture B was supplemented with 1 µl of deoxynucleotide triphosphate α-$^{32}$PdATP (10 µCi/µl). The reaction mixture was assembled at room temperature and incubated at 16° C. for 2 hours. Two aliquots of 2.0 µl each were removed for TCA precipitation and alkaline gel analysis. Two micrograms of oyster glycogen were added to the remaining reaction mixture, followed by 5.0 µl of 0.5M EDTA and 200.0 µl TE pH 7.4. The reactions were phenol-chloroform extracted and ammonium acetate precipitated.

Reaction mixtures A and B were each resuspended in 36.0 µl sterile, distilled water. The single-stranded DNA in the hairpin structure was cleaved using a mung bean nuclease reaction mixture that contained 6.0 µl of 10×× S1 buffer (300 mM NaAc pH 4.6, 3M NaCl, 10 mM $ZnSO_4$), 6.0 µl of 10 mM dithiothreitol, 1.0 µl of 50% glycerol, 6.0 µl mung bean nuclease (NEB, Beverly, Mass.). The reactions were incubated for 30 minutes at 30° C. and terminated by dilution to 100.0 µl with TE pH 7.4. Two microliters were removed for alkaline gel analysis. An additional 50.0 µl of 2M Tris pH 7.4 and 50.0 µl TE pH 7.4 were added. The mixtures were phenol-chloroform extracted twice and chloroform extracted once. The reaction mixtures were precipitated using 60.0 μl 8M NH₄Ac and 260.0 μl isopropanol and the pellets were washed in 80% ethanol.

After the mung bean nuclease digestion the DNA was blunted with T4 DNA polymerase treatment. The cDNA was resuspended in 24.0 μl sterile, distilled water; to which 10×T4 polymerase buffer (330 mM Tris acetate pH 7.9, 670 mM potassium acetate, 100 mM magnesium acetate and 1 mg/ml gelatin), 4.0 μl of each 1 mM deoxynucleotide triphosphate, 4.0 μl of 50 mM dithiothreitol and 4.0 μl of 14 μu/μl T4 DNA polymerase was added and incubated at 15° C. for 60 minutes. After terminating the reaction by addition of 200.0 μl of TE, the reaction was phenol/chloroform extracted. The cDNA was precipitated using ammonium acetate and isopropanol.

Plasmid Zem228 is a pUC18-based expression vector containing a unique Bam HI site for insertion of cloned DNA between the mouse metallothionein-1 promoter and SV40 transcription terminator and an expression unit containing the SV40 early promoter, neomycin resistance gene, and SV40 terminator. Plasmid Zem228 was modified to delete the two Eco RI sites by partial digestion with Eco RI, blunting with DNA polymerase I (Klenow fragment) in the presence of dNTPs, and re-ligation. Digestion of the resulting plasmid with Bam HI followed by ligation of the linearized plasmid with Bam HI-Eco RI adapters resulted in a unique Eco RI cloning site. The resultant plasmid was designated Zem228R. The Sst I site between the SV40 promoter and the mouse metallothionein-1 promoter was destroyed by linearizing Zem228R with Sst I, blunting the adhesive ends with T4 DNA polymerase in the presence of dNTPs and religating the linearized, blunt-ended fragment. A plasmid in which the Sst I site was destroyed was designated Zem228Ra.

In order to facilitate directional insertion of cDNA fragments into Zem288Ra, an adapter was synthesized which contained a 5' Eco RI adhesive end, an internal Sst I site and a 3' Eco RI adhesive end that does not regenerate an Eco RI site upon ligation with an Eco RI adhesive end. Plasmid Zem228Ra was linearized by digestion with Eco RI, and the linearized plasmid was treated with calf alkaline phosphatase to prevent recircularization. The linearized plasmid was ligated with kinased oligonucleotides ZC3168 and ZC3169 (Sequence ID Nos. 13 and 14; respectively). A plasmid containing inserted adapter was designated Zem228C.

To improve the ability achieve an Eco RI+ Sst I cleavage of the Zem228C vector, an oligonucleotide adapter was synthesized that contained an internal Eco RI site flanked by Eco RI adhesive ends that do not regenerate Eco RI sites upon ligation with Eco RI adhesive ends. Oligonucleotides ZC1773 and ZC1774 (Sequence ID Nos. 5 and 6, respectively) were kinased and annealed to form the adapter. Plasmid Zem228C was linearized by digestion with Eco RI, and the linearized vector and kinased adapter were ligated. A plasmid containing adapter was confirmed and sequenced. Sequence analysis revealed that the plasmid contained a 30 bp DNA insert between the new Eco RI site and the downstream Sst I site. Since an Eco RI+ Sst I cleavage of the vector prior to the insertion of a cDNA sequence removes the additional DNA sequence, the inserted DNA was not removed. The plasmid was designated Zem1698 (also referred to as Zem228CC).

To facilitate the cloning of the cDNA into vector Zem1698, EcoRI adapters (Invitrogen, San Diego, Calif.) were ligated to the cDNA. The cDNA was resuspended in 24.0 μl of sterile, distilled water and 4.0 μl of 10× ligase buffer (500 mM Tris-HCl pH 7.8 and 50 mM MgCl₂), 2.0 μl of 10 mM dATP, 2.0 μl of 200 mM dithiothretiol, 4.0 μl of 1 μg/μl adaptor DNA and 4.0 μl of 1 Weiss U/μl T4 ligase (Boehringer Mannheim, Indianapolis, Ind.) were added to the DNA solution. The ligation reaction was incubated overnight at room temperature. The ligase was heat inactivated by incubation at 65° C. for 10 min. The cDNA was digested with SstI for 8 hrs in a 200 μl reaction with 20 units of SstI and isopropanol precipitated.

To size fractionate the cDNA and remove linkers the cDNA was subjected to chromatography using a Sepharose 2B-CL column with 10 mM Tris-HCl, pH 7.4, and 0.1 mM EDTA as the column buffer. The DNA in the void volume was collected and ethanol precipitated. The final yield of cDNA was 1.9 μg.

The cloning vector Zem1698 was treated with alkaline phosphatase to prevent recircularization of the vector. The cDNA included hemiphosphorylated EcoRI linker adaptors, as described previously, and was phosphorylated using the following reaction to allow for cloning into the Zem1698 vector. Twenty-five microliters of 80 ng/μl was mixed with 1 μl of 200 mM dithiothreitol, 5 μl of 10 mM adenosine triphosphate, 5 μl of 10× T4 Kinase buffer (700 mM Tris-HCl pH 7.6, 1M KCl, 100 mM MgCl₂) and 5 μl of 10 U/μl T4 polynucleotide kinase (GIBCO-BRL, Gaithersburg, Md.). The reaction mixture was incubated for 45 minutes at 37° C., followed by a 10 minute incubation at 65° C. TE was added to a final volume of 150 μl and the reaction mixture was phenol-chloroform extracted once and chloroform extracted once. The cDNA was precipitated with sodium acetate and ethanol. The cDNA was resuspended to a final concentration of 80 ng/μl.

Test ligations demonstrated that 10 ng of cDNA and 40 ng of vector were optimal for expressing the cDNA library. The ligation reaction was scaled up using 8 μl of vector Zem1698 digested with EcoRI and SstI and 2 μl of 80 ng/μl cDNA and was reacted in a 80 μl reaction volume containing: 1 μl 10× ligase (500 mM Tris-HCl pH 7.8, 100 mM MgCl₂, 250 μg/ml BSA), 0.5 μl of 10 mM dithiothreitol and 1 μl of 1 μg/ml mussel glycogen. The reaction was incubated at room temperature for 12 hours, after which time, 40 μl of water, 4 μl of 2M Tris pH 8.0 and 4 μl of 0.5M EDTA were added. The reaction was phenol/chloroform extracted and precipitated with ammonium acetate and ethanol. The pellet was rinsed in 70% ethanol and resuspended in 20 μl water.

One microliter of cDNA was used to transform Electromax® E. coli cells (GIBCO-BRL, Gaithersburg, Md.) using a Gene Pulser® with a Pulse Controller® (Bio-RAD, Richmond, Calif.) set to 25 μF, 2.3 KV, 400 ohms and using a cuvette with a 2 mm gap. After electroporation the cells were resuspended in 1 ml of LB broth and plated at 1:10,1:100 and 1:1000 dilutions onto LB plates with 100 μg/ml ampicillin. The plates were incubated overnight at 37° C. and the titer was determined. The remaining cDNA was concentrated to 8 μl and 4 independent electroporation reactions using 2 μl of cDNA per 25 μl of cells were done as described above. The 4 electroporation reactions were pooled into a single mixture in LB broth with a final volume of 8.2 ml and incubated for 30 minutes at 37° C. in a roller drum. The inoculum was plated (200 μl/plate) on 40 15-cm LB and ampicillin plates as described above. Titering of the plates determined each plate had approximately 208,000 colonies. The plates were scraped to remove the cells and the plasmid DNA was isolated.

II. Isolation of Calcitonin Receptor cDNA by PCR Amplification

T-47D human breast carcinoma double-stranded cDNA was used as a template for the amplification of calcitonin receptor sequences using degenerate oligonucleotides (ZC4698 and ZC4699; Sequence ID Nos. 11 and 12, respectively) corresponding to regions of high conservation and low degeneracy based on a multiple alignment of the porcine calcitonin receptor, the rat secretin receptor and the opossum parathyroid hormone receptor. A 50 µl reaction was set up containing 80 ng of template cDNA; 100 pmole each of oligonucleotides ZC4698 (Sequence ID No. 11) and ZC4699 (Sequence ID No. 12); 5 µl of 10× PCR buffer (Promega Corp., Madison, Wis.); 5 µl of each 2.5 mM deoxynucleotide triphosphate; 0.25 µl of Taq polymerase (Promega) and 29.75 µl of water. The polymerase chain reaction was run for 2 cycles at 94° C. for 90 seconds, 40° C. for 90 seconds and 72° C. for 120 seconds; 38 cycles at 94° C. for 45 seconds, 50° C. for 45 seconds, 72° C. for 120 seconds, followed by a 7 minute incubation at 72° C.

The reaction mixture was electrophoresed on a 1.2% agarose gel and a DNA fragment of approximately 600 base pairs was isolated, phenol-chloroform extracted and resuspended in 15 µl water. The 600 bp fragment was amplified using the polymerase chain reaction. The reaction mixture contained 1 µl of 600 bp template, 100 pmole of each oligonucleotide (ZC4698, Sequence ID No. 11 and ZC4699, Sequence ID No. 12), 5 µl of 10× PCR buffer (Promega), 5 µl of each 2.5 mM deoxynucleotide triphosphate and 0.6 µl of Taq polymerase (Promega). The reaction was run as follows: 2 cycles at 90° C. for 90 seconds, 45° C. for 45 seconds, 72° C. for 120 seconds; 30 cycles at 94° C. for 45 seconds, 45° C. for 45 seconds, 72° C. for 120 seconds and terminated with a 7 minute incubation at 72° C. The reaction mixture was cooled at 4° C. and electrophoresed on a 1% low melting agarose gel. A 600 bp fragment was excised and purified.

The 600 bp fragment was cloned into the prime2 vector. The prime2 vector was constructed by inserting the oligonucleotides ZC.4418 and ZC.4419 (Sequence ID No. 9 and Sequence ID No. 10, respectively) into the PstI restriction site of the phagemid vector pBluescript I (Stratagene, La Jolla, Calif.) This destroyed the original PstI site and created a new PstI site in the center of the oligonucleotide insert. The prime2 vector was digested to completion with PstI resulting in a 3' overhang. Cohesive ends were generated for the vector and the insert in separate reactions each containing 0.5 µg prime2 vector or 4 µl of the 600 bp insert DNA fragment, 2 µl of 10× bacteriophage T4 DNA polymerase buffer (Sambrook et al., *Molecular Cloning, A Laboratory Manual*, 2d ed., Cold Spring Harbor Laboratory Press, Cold Spring Harbor, N.Y., 1989, which is incorporated herein by reference), 2 µl of each 1 mM dGTP or dCTP, 2 µl of T4 DNA polymerase.

A ligation reaction of the prime2 vector and 600 bp DNA fragment included 1 µl of prime2 vector, 10 µl of the 600 bp DNA fragment, 3 µl of 10× ligation buffer (Boehringer Mannheim), 3 µl of ligase (NEB, Beverly, Mass.) and 30 µl of water. After overnight incubation at room temperature, the reaction mixture was phenol-chloroform extracted. Once ethanol precipitated, the DNA was resuspended in 25 µl water.

The resulting plasmid, designated 600/prime2, was used to transform *E. coli* strain DH10B ELECTROMAX cells (GIBCO BRL) by electroporation. One transformant, designated 600/prime2#1, was selected and plasmid DNA was isolated. Sequence analysis showed that the insert encoded a polypeptide related to the porcine calcitonin receptor.

III. Cloning Full-Length Human Calcitonin Receptor From Breast Carcinoma cDNA A full length human calcitonin receptor cDNA was obtained by screening the JT47d library described in Example I. The JT47d library was plated onto 39 150-mm petri dishes containing LB +70 µg/ml ampicillin at a density of $2 \times 10^5$ colony forming units (cfu). Enough LB broth was added to each plate to make a suspension of the colonies. The cell suspensions were designated 1–39 and placed in LB with 15% glycerol added and frozen at −80° C. Vials containing cell suspensions 1–4 were thawed on ice. One microliter of each suspension was diluted into 10 ml of LB broth and plated at 1, 10 or 100 µl per 150 mm plate containing LB+ ampicillin, prepared by covering each plate with a 137 mm, 1.2 µm BIOTRANS nylon filter (ICN, Irvine, Calif.). The plates were incubated for 12 hours at 25° C., followed by a 5 hour incubation at 37° C., until the colonies were approximately 0.5 mm in size. Replicate copies of the master filter were made by pressing fresh nylon filters onto the master, placing the layers between 3 mm Whatman paper and 2 glass plates and applying pressure to the top plate. The filters were keyed for orientation using an 18 gauge needle. The screening copies were placed on 150 mm LB+170 µg/ml chloramphenical plates and incubated at 37° C. for 3 days. The master filter was placed on a 150 mm LB+70 µg/ml ampicillin plate and incubated for several hours at 37° C. The master filter was removed and stored at 4° C. Approximately 400,000 colonies were screened.

The plasmid 600/prime2#1 was prepared for use as a probe by first digesting with EcoRI and BamHI. The DNA fragment was twice gel purified, using a 2.5% agarose gel and 1% low-melting agarose gel, respectively. A band of approximately 600 bp was isolated. Approximately 30 ng of the 600 bp DNA fragment was radiolabeled using αdCTP and the Stratagene Prime-It Kit (Stratagene) according to the manufacturer's specifications.

The cDNA filters were prehybridized in 80 ml of a solution of 50% formamide, 5 ml of 100× Denhardt's solution (Sambrook, ibid.), 5 ml of 10% SDS, 30 ml of 20× SSC. (Sambrook, ibid.) and water to make a final volume of 100 ml. After incubating at 37° C. overnight, new hybridization solution with 8.6 g Dextran Sulfate and 1.8 ml of boiled 10 mg/ml salmon sperm DNA was added. The 600/prime2#1 probe was boiled to denature and $8.6 \times 10^7$ cpm of labeled probe were added to the filters and hybridization solution. The filters were hybridized overnight at 37° C.

One clone hybridized to the probe and was rescued from the master filter. The section of the filter corresponding to the positive signal was removed and placed in 2 ml LB broth and vortexed. The culture was replated at several serial dilutions on new filters and processed as described above. Labeled probe 600/prime2#1 was used to screen the new filters and verified that the clone hybridized to the probe. This clone was designated pHollex and has been deposited with the American Type Cell Culture, Rockville, Md. as an *E. coli* XLI blue transformant under Accession No. 69067. Sequence analysis, and restriction analysis revealed that the cDNA had an insert of 3.3 kb. The coding sequence was 1422 bp with an 3' untranslated sequence of 1.9 kb. Hollex encoded a protein of 474 amino acids, and had 70.3% amino acid identity to the porcine calcitonin receptor.

IV. Identification of a Truncated Human Calcitonin Receptor From ovarian cDNA Human ovary first-strand cDNA was obtained from Clontech (Palo Alto, Calif.) and used as a template for the amplification of calcitonin receptor sequences by polymerase chain reaction, using oligonucleotides (ZC5471 and ZC5468; SEQ ID NO: 16 and 17, respectively) corresponding to regions of human calcitonin receptor (as shown in SEQ ID NO: 1). A 50 µl reaction was set up containing 1 ng template DNA, 5 µl (100 pmoles) of each oligonucleotide ZC5468 and ZC5471 (SEQ ID NO: 17 and 16, respectively), 5 µl of each 2.5 mM deoxynucleotide triphosphate, 5 µl of 10× VENT$_R$ buffer (100 mM KCl, 200 mM Tris-HCl pH8.8, 100 mM $(NH_4)_2SO_4$, 20 mM $MgSO_4$ and 1% Triton X-100 (polyethylene glycol 4-isooctylphenyl ether) (New England Biolabs)), 0.5 µl of VENT$_R$ thermostable DNA polymerase (New England Biolabs) and 29.5 µl of water. The polymerase chain reaction was run for 2 cycles at 94° C. for 90 seconds, 58° C. for 90 seconds and 72° C. for 2 minutes; 38 cycles at 94° C. for 45 seconds, 58° C. for 45 seconds and 72° C. for 2 minutes; followed by 1 cycle at 72° C. for 7 minutes and stored at 4° C. overnight.

The reaction mixture was electrophoresed on a 2% agarose gel and a DNA fragment of approximately 600 base pairs was isolated. The agarose containing the DNA was crushed to form an aqueous solution. The resulting DNA fragment was used as template for a polymerase chain reaction using oligonucleotides (ZC5469 and ZC5474, SEQ ID NO: 18 and 19, respectively) which were designed to hybridize to sequences located internally to oligonucleotides ZC5471 and ZC5468 (SEQ ID NO: 16 and 17, respectively). A 50 µl reaction was set up containing 1 µl template DNA, 5 µl (100 pmoles) of each oligonucleotide ZC5469 and ZC5474 (SEQ ID NO: 18 and 19, respectively), 5 µl of each 2.5 mM deoxynucleotide triphosphate, 5 µl of 10× VENT$_R$ buffer (New England Biolabs), 0.5 µl of VENT$_R$ polymerase (New England Biolabs) and 29.5 µl of water. The polymerase chain reaction was run for 2 cycles at 94° C. for 90 seconds, 58° C. for 90 seconds and 72° C. for 2 minutes; 28 cycles at 94° C. for 45 seconds, 58° C. for 45 seconds and 72° C. for 2 minutes; followed by 1 cycle at 72° C. for 7 minutes and stored at 4° C. overnight.

The reaction mixture was electrophoresed on a 1% agarose gel, and a DNA fragment of approximately 400 base pairs was seen. A 35 µl aliquot of the polymerase chain reaction amplification was electrophoresed on a 1% low melt agarose gel, and the 400 base pair fragment was excised and suspended in an equal volume of 1×TBE. The fragment was purified using phenol-chloroform extraction and resuspended in 10 µl water.

The polymerase chain reaction generated a blunt-ended DNA fragment. Using a blunt-ended SmaI restriction digested pUC19 vector, a ligation reaction was set up containing 3 µl DNA, 2 µl pUC19, 3 µl 10× ligase buffer, 3 µl ligase and 19 µl water. One microliter aliquots were used to electroporate ELECTROMAX DH10B *E. coli* cells (GIBCO-BRL, Gaithersburg, Md.) using a Gene Pulser with a Pulse Controller (Bio-Rad, Richmond, Calif.) set to 25 µF, 2.3 KC, 400 ohms and using a cuvette with a 2 mm gap. After electroporation the cells were resuspended in 1 ml of LB broth and plated onto LB plates containing 100 µg/ml ampicillin at 10 µl, 100 µl and 890 µl dilutions. The plates were incubated overnight at 37° C. Replicate filters were prepared by covering and carefully removing 2 1.2-1M filters (ICN, Irvine, Calif. from each petri dish. The filters were keyed for orientation using an 18 gauge needle and baked for 1 hour at 80° C. After drying, the filters were placed in 50 ml of prehybridization solution that contained 50% formamide, 5 ml of 10% SDS, 5 ml of 100× Denhardt's solution (USA Biochem. Corp., Cleveland, Ohio.), 30 ml of 20× SSC. (Sambrook, ibid.), 50 ml of 0.2 mg/ml salmon sperm DNA and water to make a final volume of 100 ml. The filters were placed at 37° C. to incubate overnight.

The oligonucleotide ZC5162 (SEQ ID NO: 21), which hybridizes to a portion of the human calcitonin receptor within the 400 base pair fragment, was prepared for use as a probe by radiolabelling the DNA using α-dCTP and the Stratagene Prime-It Kit (Stratagene) according to the manufacturer's specifications.

The prehybridization solution was removed, and 50 ml of new hybridization solution containing $10^6$ cpm/ml of the probe ZC5162 (SEQ ID NO: 21) was added to the filters. The filters were hybridized overnight at 37° C. The probe hybridized to four clones, all located on the filter from the 890 µl plating. Three of the four colonies were isolated and inoculated into 5 ml 2× YT broth (16 g. of Bacto Typtone (DIFCO, Detroit, Mich.), 10 g. of Yeast Extract (DIFCO), 10 g. of NaCl and water to 1 liter) that included 100 µg/ml ampicillin. The cultures were grown overnight at 37° C., and plasmid DNA was isolated. The plasmid DNA was digested with EcoRI and HindIII and electrophoresed on an agarose gel to verify inserts of the correct size. All three clones had inserts of 400 base pair size. The clones were streaked out on LB plates containing 100 µg/ml ampicillin to isolate pure colonies, and the plasmid DNA isolation and restriction digests were repeated as described above. The DNA was analyzed on a 2.5% agarose gel, and the 400 base pair insert was verified.

Sequence analysis of the cDNA fragment indicated that the sequence was identical to the clone designated Hollex 1 with the exception of a 35 base pair insert beginning after nucleotide 572 (see SEQ ID NO: 1) that resulted in a frame shift. The nucleotide and deduced amino acid sequence of the ovarian calcitonin receptor cDNA clone is shown at SEQ. ID NO.24 and SEQ ID NO.25

V. IDENTIFICATION OF A FULL-LENGTH HUMAN CALCITONIN RECEPTOR PLACENTAL cDNA

Human placental first strand cDNA was obtained from Clontech (No. 7116-1) and used as a template for amplification of calcitonin receptor sequences by polymerase chain reaction using oligonucleotides (ZC5471 and ZC5468; SEQ ID NO: 16 and 17, respectively) corresponding to regions of human calcitonin receptor as described previously. A 50 µl reaction was set up containing 1 µl (1 ng/µl) of template cDNA, 5 µl of (100 pmoles) each oligonucleotide ZC5471 and ZC5468 (SEQ ID NO: 16 and 17, respectively), 5 µl of each 2.5 mM dNTP, 5 µl of 10× VENT$_R$ buffer (New England Biolabs), 0.5 µl of VENT$_R$ polymerase (New England Biolabs) and 29.5 µl of water. The polymerase chain reaction was run for 2 cycles at 94° C. for 90 seconds, 60° C. for 90 seconds and 72° C. for 2 minutes; 38 cycles at 94° C. for 45 seconds, 60° C. for 45 seconds and 72° C. for 2 minutes; followed by 1 cycle at 72° C. for 7 minutes and stored at 4° C. overnight. Ten microliters of the polymerase chain reaction product was analyzed by gel electrophoresis. The reaction product was approximately 600 base pairs.

The reaction mixture was electrophoresed on a 1% agarose gel, and a DNA fragment of approximately 600 base pairs was isolated by excising the agarose containing the DNA fragment from the rest of the gel. The agarose was crushed to form an aqueous solution and used as template for a polymerase chain reaction. The template DNA was amplified in a reaction that contained 1 µl of template cDNA, 5 µl (100 pmoles) of each oligonucleotide ZC5471 and ZC5468 (SEQ ID NO: 16 and 17, respectively), 5 µl of each 2.5 mM dNTP, 5 µl of 10× VENT$_R$ buffer (New England Biolabs), 0.5 µl of VENT$_R$ polymerase (New England Biolabs) and 29.5 µl of water. The polymerase chain reaction was run for 2 cycles at 94° C. for 90 seconds, 60° C. for 90 seconds and 72° C. for 2 minutes; 38 cycles at 94° C. for 45 seconds, 60° C. for 45 seconds and 72° C. for 2 minutes; followed by 1 cycle at 72° C. for 7 minutes and stored at 4° C. overnight.

The reaction mixture was electrophoresed on a 2% gel, and four DNA bands ranging from 500 to 800 base pairs were seen. Each of the four bands was excised, purified using a 1.5% agarose gel, phenol-chloroform extracted and ethanol precipitated, and each DNA pellet was resuspended in 5 μl water.

Each of the four DNA fragments was phosphorylated to facilitate cloning into the blunt-ended, dephosphorylated vector pNEB193 (a pUC19 derivative obtained from New England Biolabs) in a reaction mixture containing: 4 μl of approximately 10 ng/μl of DNA fragment; 5 μl of 0.01M $^{32}$P gamma-ATP; 5 μl of 10× polynucleotide kinase buffer (700 mM Tris-HCl pH7.8, 100 mM $MgCl_2$ and 50 mM dithiothereitol (New England Biolabs)), 5 μl of polynucleotide kinase (New England Biolabs) and 33.5 μl of water. The reaction mixture was incubated at 37° C. for 1 hour followed by a 45 minute incubation at 65° C. Each of the four phosphorylated DNA fragments was ligated with pNEB193 by adding to the phosphorylation reaction mixture 1 μl of 250 mM dithiothreitol, 1 μl of approximately 30 ng/μl SmaI linearized pNEB193 and 2.5 μl of T4 DNA ligase (New England Biolabs). The reaction mixture was incubated at room temperature for 20 minutes. Following the incubation, 5 μl of 10× ligation buffer (New England Biolabs), 40 μl of water and 5 μl of T4 DNA ligase were added, and the reaction mixture was incubated at room temperature. The ligated DNA was purified by phenol-chloroform extraction and ethanol precipitation, and the DNA was resuspended in 20 μl water. The plasmid DNA was digested with SmaI, phenol extracted and resuspended in 5 μl of water. The linearized DNA was used to electroporate ELECTROMAX DH10B E. coli cells as described previously. The cell mixture was resuspended in 1 ml of LB broth and was used to inoculate LB plates containing 100 μg/ml ampillicin, 60 μl 50 mg/ml Xgal and 20 μl of 100 mM IPTG. The plates were incubated at 37° C. overnight, and seven white colonies from each of the four different DNA fragments were selected for culturing.

Twenty-eight selected colonies were individually inoculated into 5 ml of 2× YT broth and grown overnight at 37° C. Plasmid DNA was isolated and digested with EcoRI and HindIII restriction enzymes. One microliter of each restriction digest was run on a 2.5% agarose gel. The DNA was transferred to nitrocellulose, and the blot was probed essentially as described by Southern (J. Mol. Biol. 98:503, 1975; Sambrook et al., ibid.) with a 3.3 kb Bam HI fragment from pHollex that included the entire coding region of the human calcitonin receptor. The pHollex fragment was radiolabeled using a Multiprime DNA labeling kit (Amersham, Arlington Heights, Ill.), according the manufacturer's specifications.

Six of the 28 clones hybridized to the human calcitonin receptor probe and were selected for sequence analysis. The analysis revealed that one clone, designated pla 14, had a 9 base pair insert but did not appear to be a pure culture. The clone pla 14 was purified by streaking the mixed culture on a LB plate that contained 100 μg/ml ampillicin. Six colonies were isolated and subjected to sequence analysis. These colonies were designated pla 14.1–14.6. Two of these clones, pla 14.4 and pla 14.6, each had a 9 base pair insert. The clone pla 14.6 was used as the source for plasmid DNA and following plasmid DNA isolation was digested with EcoRI and NsiI. The DNA was electrophoresed on a 2.5% agarose gel, and a 150 base pair fragment was isolated and purified using phenol-chloroform extraction and ethanol precipitation. The DNA was resuspended in 31 μl of water.

The nucleotide sequence and deduced amino acid sequence of the placental calcitonin receptor clone is shown at SEQ ID N0.26 and SEQ ID NO.27

EXAMPLE II

Expression of Human Calcitonin Receptor in Mammalian Cells

This Example describes the expression of functional human calcitonin receptor by cells in a manner that was capable of binding calcitonin, activating adenylate cyclase activity, and increasing intracellular calcium.

A. TRANSFECTION INTO LUCIFERASE CELL LINE

The human calcitonin receptor cDNA pHollex was expressed in a BHK570 cell line stably transfected with pKZ10, an expression unit comprising a promoter containing two cyclic AMP response elements, the luciferase cDNA and the hGH terminator. This cell line permits the measurement of luciferase activity, adenylate cyclase activity and intracellular calcium concentrations in response to calcitonin binding to its receptor.

The enkephalin cyclic AMP response element (CRE) in plasmid ZK6 was obtained from Zem233. Zem233 was derived from plasmids Zem67 and Zem106. Plasmid Zem106 was constructed from the precursor Zem93. To construct Zem93, a Kpn I-Bam HI fragment comprising the MT-1 promoter was isolated from MThGH111 (Palmiter et al., Science 222:809–814, 1983) and inserted into pUC18. Plasmid Zem93 was then digested with Sst I and re-ligated to generate plasmid Zem106, in which approximately 600 bp of sequence 5' to the MT-1 promoter were eliminated.

An enkephalin CRE was inserted into Zem106 by first digesting Zem106 with EcoRI and SstI to isolate the vector-containing fragment. Oligonucleotides ZC982 and ZC983 (Sequence ID Nos. 3 and 4, respectively) were designed to encode when annealed a proenkephalin CRE from nucleotides –71 to –133 (Comb et al., Nature 323:353–356, 1986) flanked by a 5' EcoRI site and a 3' SstI site. Oligonucleotides ZC982 and ZC983 (Sequence ID Nos. 3 and 4, respectively) were kinased, annealed and ligated with the linearized Zem106 to obtain plasmid Zem224.

Plasmid Zem67 was obtained by first digesting pIC19R (Marsh et al., Gene 32:481–486, 1984) with SmaI and HindIII. The ori region of SV40 from map position 270 (Pvu II) to position 5171 (Hind III) was then ligated to the linearized pIC19R to produce plasmid Zem67. The HindIII-BamHI neomycin resistance gene-SV40 terminator fragment from plasmid pSV2-neo (available from ATCC as Accession no. 37149) was inserted into Hind III-Bgl II digested Zem67 to obtain Zem220.

The SV40 promoter-neomycin resistance gene-SV40 terminator expression unit from plasmid Zem220 was isolated as an Eco RI fragment. Plasmid Zem224 was digested with Eco RI and treated with calf alkaline phosphatase to prevent recircularization. The neomycin expression unit and the linearized Zem224 were ligated. A plasmid containing the SV40 promoter proximal to the CRE was designated Zem233.

Plasmid Zem233 was modified to insert an additional CRE sequence, a TATA box, and a portion of the lacZ coding and poly(A) sequences immediately 3' to the proenkephalin CRE sequence such that the resulting expression unit was in the opposite orientation relative to the neomycin resistance expression unit present in Zem233. Plasmid Zem233 was linearized by digestion with SstI and BamHI. Oligonucleotides ZC3509 and ZC3510 (Sequence ID Nos. 7 and 8, respectively) were designed such that when annealed, the resulting duplex encodes a glycoprotein CRE (Delegeane et al., *Mol. Cell. Biol.* 7:3994–4002, 1987) with a 5' SstI adhesive end and a 3' EcoRI adhesive end. The oligonucleotides were annealed according to standard Procedures. The thymidine kinase TATA box was obtained as an Eco RI-Pst I fragment spanning nucleotides −79 to +18 of the thymidine kinase gene (McKnight *Cell* 31:355–366, 1982). The 3' sequence of the lacZ gene and its associated poly(A) sequence were obtained as a Pst I-Bam HI fragment from plasmid pLacF (obtained from Jaques Peschon, Immunex Corp., Seattle, Wash.), which contains the lacZ coding region and mouse protamine terminator sequence cloned into the pUC18 vector. The Sst I-Bam HI linearized Zem233, the Sst I-Eco RI ZC3509/ZC3510 adapter, the Eco RI-Pst I TATA box fragment and the Pst I-Bam HI lacZ sequence were ligated. A plasmid containing the expression unit in the correct orientation relative to the neomycin resistance gene expression unit of Zem233 was designated KZ5.

The luciferase gene and human growth hormone (hGH) terminator sequences were used to replace the lacZ coding and poly(A) sequences present in KZ5. The luciferase gene was initially obtained from plasmid a-1681uc (Delegeane et al., *Mol. Cell. Biol.* 7:3994–4002, 1987 and deWet et al., *Mol. Cell. Biol.* 7:725–737, 1987) as a 1.7 kb Xho I-Xba I fragment. The hGH terminator was obtained as an Xba I-Sal I fragment from Zem219b (deposited as an *E. coli* transformant with the ATCC under Accession no. 6879). The luciferase gene and hGH terminator sequences were subcloned into Xho I-Sal I linearized pIC19H (Marsh et al., ibid.) for convenience. The resulting plasmid, KZ8, was digested with Xho I and Sal I to isolate the luciferase-hGH terminator sequences. Plasmid KZ5 was digested with Sal I to isolate the vector-containing fragment and was treated with calf alkaline phosphatase to prevent recircularization. The Xho I-Sal I luciferase-hGH terminator fragment was ligated with the Sal I-digested KZ5. A plasmid containing the luciferase-hGH terminator in the proper orientation relative to the promoter was designated KZ6.

Plasmid KZ6 was digested with HindIII to remove a DNA fragment containing the SV40 promoter, CRE unit, Luciferase gene, human growth hormone gene and poly(A) sequences. Zem 219b (ATCC accession number 68979) was digested with HindIII to isolate the DHFR gene and pUC18 sequences. The KZ6 and Zem219b DNA fragments were gel purified isolated as a 3.0 kb fragment and a 5.0 kb fragment, respectively, and ligated. The resulting plasmid containing a CRE-responsive luciferase gene and a DHFR selectable marker was designated plasmid KZ10.

Plasmid KZ10 was transfected into BHK570 cells (available from ATCC as Accession no. CRL 10314) using the calcium phosphate precipitation method essentially as described by Graham and Van de Eb (*Virol.* 52:456, 1973, which is incorporated by reference herein). The transfected cells were grown in growth medium (Dulbecco's modified Eagle's medium (DMEM) containing 10% fetal calf serum and 2.0 mm L-glutamine). After a few days in nonselective growth medium, the growth medium was replaced with methotrexate (MTX) selection medium (growth medium containing 250 nM MTX). The cells were then allowed to grow to confluency after which they were trypsinized and plated at limiting dilution into the wells of 96-well plates. The cells were grown for one to two weeks in methotrexate selection medium. Clones from wells containing single colonies were assayed for the ability to respond to forskolin in the luciferase assay described below. Forskolin elevates the cellular cAMP level and thus the associated cAMP-dependent biological response pathways in a receptor-independent manner. A clone capable of responding to forskolin was designated BHK/KZ10-20-48.

B. EXPRESSION OF THE OVARIAN CALCITONIN RECEPTOR cDNA

Oligonucleotide primers ZC5468 and ZC5471 (SEQ ID NO: 17 and 16, respectively) were used for the amplification of the ovarian calcitonin receptor cDNA and contained a 3' EcoRI restriction site and a 5' NsiI restriction site. These restriction sites were used to remove the ovarian cDNA from the polymerase chain reaction generated clones and insert the DNA fragment into the corresponding region of pHollex, creating a new plasmid containing the calcitonin receptor with the ovarian cDNA insertion. Two of the ovarian clones, designated 6 and 7, were pooled and digested with EcoRI and NsiI. The cDNA fragment was excised, then analyzed and isolated using a 2.5% agarose gel, and found to be 180 base pairs. To facilitate cloning of the ovarian cDNA 180 base pair fragment, a BglII/BclI portion (1.5 kb) of the clone pHollex was ligated into the cloning vector pNEB193 (New England Biolabs) by digesting pNEB193 with EcoRI and SmaI and making the plasmid blunt-ended using the Klenow fragment of DNA polymerase. The pNEB193 DNA was digested with BamHI and ligated with a BglII/BclI (BamHI compatible) fragment of pHollex. The resulting plasmid, pHollex/NEB193, has a 3' EcoRI restriction site and a 5' NsiI restriction site surrounding the calcitonin receptor cDNA. Twenty-five micrograms of the plasmid was digested with EcoRI and NsiI, and a 4.5 kb fragment was isolated by gel purification using a 0.8% agarose gel. The resulting fragment was resuspended in 60 µl of water. The ovarian cDNA fragment and pHollex linearized plasmid were ligated in a reaction mixture containing 1 µl of approximately 50 ng/µl pHollex; 1 µl of approximately 10 ng/µl ovarian calcitonin receptor cDNA; 3 µl 10× ligation buffer; 3 µl T4 ligase (New England Biolabs) and 22 µl water. The reaction mixture was incubated at room temperature for approximately 3 hours, phenol-chloroform extracted and ethanol precipitated. The resulting DNA pellet was resuspended in 5 µl water, and 1 µl ligated DNA was used to electroporate ELECTROMAX DH10B *E. coli* cells as described above. The cells were plated on LB plates containing 100 mg/ml ampicillin, and 18 colonies were isolated. Cultures were grown from these colonies, and plasmid DNA was isolated. The clones were designated Ovex 1–18, and each clone was shown to contain a 1.5 kb insert using gel analysis. Sequence analyses of Ovex clones 1 and 2 revealed a 35 base pair insert in the calcitonin cDNA identical to the original fragment generated by the polymerase chain reaction amplification.

Ovex 1 and 2 were subcloned into mammalian expression vector Zem228R. Vector Zem228R is a precursor of Zem1698 described in Example I.I. Plasmid Zem228R was digested with EcoRI to linearize the vector and made blunt-ended in a reaction that contained 10× nick translation buffer (0.5M Tris-HCl pH7.2, 0.1M $MgSO_4$, 1 mM dithiothreitol, 500 µg/ml bovine serum albumin), 2.5 mM of each dNTP, 5 µl of the Klenow fragment of DNA polymerase (GIBCO-BRL), 10 µl of approximately 20 ng/µl plasmid Zem228R and 50 µl water. The reaction mixture was incubated at room temperature for one hour, extracted with phenol-chloroform and ethanol precipitated. The DNA pellets were resuspended in 85 µl of water, treated with calf alkaline phosphatase and gel purified. The Ovex clones were digested with AscI and HindIII to remove the pNEB193 fragment from the insert. The resulting fragment was identified as 1.5 kb and gel purified. The 1.5 kb DNA fragment was made blunt-ended in a reaction containing: 20 µl AscI/HindIII digested ovex DNA; 10 μl 10× nick translation buffer; 5 μl of the Klenow fragment of DNA polymerase (GIBCO-BRL); 5 μl of 2.5 mM dNTPs and 60 μl water. The reaction mixture was incubated at room temperature for 30 minutes and phenol-chloroform extracted. The DNA was ethanol precipitated and resuspended in 10 μl water.

The blunt-ended, linearized vector Zem228R and blunt-ended Ovex cDNA fragment were ligated in a reaction containing: 1 μl of approximately 20 ng/μl calf alkaline phosphatase-treated Zem228R; 3 μl of 10× ligation buffer (New England Biolabs); 3 μl ligase (New England Biolabs); 5 μl AscI/HindIII blunt-ended Ovex fragment and 22 μl water. The ligation mixtures were phenol-chloroform extracted, ethanol precipitated and resuspended in 5 gml water. One microliter of ligation mixture was used to electroporate ELECTROMAX DH10B E. coli cells as described previously. The ligation-cell mixture was resuspended in 1 ml of LB broth, and 100 μl of the mixture was used to inoculate LB plates containing 100 μg/ml ampicillin.

Eighteen Ovex/Zem228R colonies were isolated and inoculated into 4 ml of 2× YT broth containing 50 μg/ml of kanamycin. The cultures were grown overnight at 37° C. Eight of the eighteen cultures grew, and these were used as a source for plasmid DNA. The plasmid DNA was digested with BamHI and gel analyzed. Each of the eight clones had an insert of the correct size (1.5 kb).

Orientation of the Ovex/Zem228R insert was determined by digesting the plasmid DNA with SalI and using gel analysis. Clones designated pOvex/Zem228R4 and pOvex/Zem228R5 were found to have the correct restriction sites.

The ovarian subtype human calcitonin receptor cDNA Ovex/Zem228R was expressed in cell line BHK/KZ10-20-48 as described in Example IIA.

C. EXPRESSION OF THE PLACENTAL CALCITONIN RECEPTOR cDNA

The vector pHollex/NEB193 was digested with NsiI and EcoRI to remove the region corresponding to the ovarian 35 base pair insert. A 4.5 kb DNA fragment was isolated and purified. A ligation reaction was prepared with a mixture containing 1 μl of 50 ng/μl EcoRI/NsiI pHollex/NEB193, 30 ng (1 μl) of the 150 base pair pla 14.6 EcoRI/NsiI DNA fragment, 3 μl of 10× ligase buffer (500 mM Tris-HCl pH 7.8, 100 mM MgCl$_2$, 100 mM dithiotheritol, 10 mM ATP and 250 μg/ml BSA (New England Biolabs)); 3 μl of ligase (New England Biolabs) and 22 μl of water. The mixture was incubated at room temperature for 3 hours followed by a phenol-chloroform extraction and ethanol precipitation. The DNA was resuspended in 5 μl of water and used to electroporate ELECTROMAX DH10B E. coli cells as described previously. Four colonies, designated plaex 1–4, were isolated and cultured, and plasmid DNA was prepared.

Confirmation of insert size was made by transferring the DNA to nitrocellulose and probing as described above. The probe was made from an oligonucleotide designed to span the 9 base pair placental clone insert (ZC5993; SEQ ID NO: 20). The probe was radiolabeled by incubation at 37° C. for 30 minutes in a mixture containing 5 μl of 3.9 pmole/μl of ZC5993 (SEQ ID NO: 20), 10 μl of 10× polynucleotide kinase buffer (New England Biolabs), 5 μl of polynucleotide kinase (New England Biolabs), 1 μl of 150 μCi/μl $^{32}$P gamma-ATP (Amersham) and 79 μl of water. The unincorporated radiolabel was removed by precipitation with spermine/salmon sperm DNA, according to the specification provided with the Multiprime DNA Labeling kit (Amersham). The nitrocellulose blots were incubated at high stringency hybridization conditions at 65° C. in 0.1× SSC/0.5% SDS (Sambrook et al., ibid.) to eliminate probe from hybridizing to clones containing the plasmid pHollex but without the placental insert. All four of the plaex clones were found to contain inserts.

One clone, designated plaex3, was subcloned into mammalian expression vector Zem228R. Zem228R was digested with EcoRI to linearize the vector and made blunt-ended as described previously. The plaex3 plasmid DNA was digested with AscI and HindIII to remove the portion of the vector corresponding to pNEB193 from the plasmid. The resulting DNA fragment was identified as 1.5 kb and gel purified. The DNA fragment was made blunt-ended as described previously.

The blunt-ended, linearized vector Zem228R and blunt-ended plaex DNA fragment were ligated in a reaction containing 1 μl of approximately 20 ng/μl phosphorylated Zem228R, 3 μl of 10× ligation buffer (New England Biolabs), 3 μl ligase (New England Biolabs), 5 μl of 50 ng/μl AscI/HindIII blunt-ended plaex DNA fragment and 22 μl water. The ligation and subsequent electroporation of ELECTROMAX DH10B E. coli cells were done as described previously. The cell mixture was resuspended in 1 ml of LB broth, and 100 μl and 900 μl aliquots of the suspension were used to inoculate LB plates containing 50 μg/ml kanamycin.

Filters were made of the plaex3 colonies using 137 mm 1.2 μM nylon membranes (ICN). The filters were dried and placed in the hybridization solution containing 62.5 ml of 20× SSPE (175.3 g NaCl 27.6 g NaH2PO4.H2O, 7.4 g EDTA, NaOH added to pH7.4 and water to 1 liter), 25 ml of 50× Denhardt's solution; 12.5 ml of 10% SDS (Sambrook et al., ibid.) and 144 ml of water with 0.2 mg/ml of boiled salmon sperm DNA added. The mixtures were incubated for several hours at 65° C. A probe was made from pHollex/NEB193 as a template and oligonucleotides ZC5470 and ZC5465 (SEQ ID NO: 22 and 23, respectively) by amplifying the DNA sequences using a polymerase chain reaction. A 50 μl reaction was set up containing 1 ng template DNA, 5 μl (100 pmoles) of each of oligonucleotides ZC5470 and ZC5465 (SEQ ID NO: 22 and 23, respectively), 5 μl of each 2.5 mM deoxynucleotide triphosphate, 5 μl of 10× VENT$_R$ buffer (New England Biolabs), 0.5 μl of VENT$_R$ polymerase (New England Biolabs) and 29.5 μl of water. The polymerase chain reaction was run for 2 cycles at 94° C. for 90 seconds, 58° C. for 90 seconds and 72° C. for 2 minutes; 38 cycles at 94° C. for 45 seconds, 58° C. for 45 seconds and 72° C. for 2 minutes; followed by 1 cycle at 72° C. for 7 minutes and stored at 4° C. overnight.

A second polymerase chain reaction was run using the product of the above reaction as the template. This reaction mixture contained 1 ng template DNA, 10 μl (200 pmoles) of each of oligonucleotides ZC5470 and ZC5465 (SEQ ID NO: 22 and 23, respectively), 10 μl of each 2.5 mM deoxynucleotide triphosphate, 4 μl of 10× VENT$_R$ (EXO−) buffer (New England Biolabs), 29.5 μl of water and a wax bead (AMPLIWAX PCR GEM 100; Perkin Elmer, Norwalk, Conn.). The reaction mixture was heated to 80° C. and the reaction carried out according to the manufacturer's specification. After incubation, 6 μl of 10× VENT$_R$ buffer (New England Biolabs), 4 μl of VENT$_R$ (EXO−) (New England Biolabs) and 50 μl of water were added to the mixture. Ten separate reaction mixtures were prepared. The polymerase chain reaction was run for 10 cycles of 94° C. for 45 seconds, 58° C. for 45 seconds, and 72° C. for 2 minutes followed by 1 cycle at 72° C. for 7 minutes. The reaction mixtures were pooled and purified by centrifugation in a Centricon 100 (Amicon, Danvers, Mass.) according to the manufacturer's specifications. The retentate was purified by ammonium acetate-2-propanol precipitation in a reaction containing 27 µl of 7.5M ammonium acetate, 55 µl of DNA supernatant, 18 µl of water and 100 µl of 2-propanol. The reaction mixture was centrifuged for 10 minutes at 14,000 rpm in an Eppendorf microcentrifuge. The pellet was resuspended in 187 µl of water to a concentration of approximately 50 ng/µl.

The filters were added to 100 ml of the hybridization solution containing $10^6$ cpm/ml of probe and incubated at 65° C. overnight. After incubation, the filters were washed 5 times in 0.1× SSC. and 0.5% SDS at 65° C. for 30 minutes per wash. Six positive colonies were identified, isolated and used to inoculate 5 ml of 2× YT broth with 100 µg/ml of ampicillin added. Plasmid DNA was isolated from the cells and analyzed by restriction digest using BamHI. All six clones were found to have the expected insert size of 1.5 kb and the clones were designated plaex 1, 2, 4. Orientation of the insert was determined by digesting the plasmid DNA with NsiI and all of the clones were found to have the correct orientation for transcription.

The placental subtype human calcitonin receptor cDNA plaex 1 was stably expressed in cell line BHK/KZ10-20-48 as described in Example IIA.

D. LUCIFERASE AND ADENYLATE CYCLASE ACTIVITY IN WHOLE CELLS pHollex or Zem1698 were used to transfect cell line BHK/KZ10-20-48 (Zem1698 transfectants were used as negative controls) as described above using calcium phosphate-mediated transfection. Transfectants were selected in a growth medium containing both 500 µg/ml G418-neomycin and 250 nM methotrexate as described previously.

Transfectants were assayed in triplicate for the induction of the CRE-luciferase response to selected agonists. Two clones, Hollex1 and Hollex2, and the vector Zem1698 (negative control) were tested. Microlite flat bottom tissue culture plates (Baxter Scientific Products, Chicago, Ill.) were set up such that each well contained $2\times10^4$ cells in 100 µl of selection media and the cells were grown overnight. The agonists were prepared in DMEM medium with 5% serum at the 2× final assay concentration containing either: $10^{-13}$ to $10^{-6}$M human calcitonin (hCT), salmon calcitonin (sCT), human calcitonin gene related peptide (hCGRP) or 20 µM forskolin (CalBiochem, San Diego, Calif.).

Induction was initiated by removing old medium from the wells and adding 100 µl of fresh growth medium and 100 µl of each 2× solution in triplicate sample wells. Uninduced levels were determined in triplicate wells to which 100 µl of DMEM containing 10% fetal calf serum was added. The plates were incubated for four hours at 37° C., 5% $CO_2$ to allow induction of luciferase.

Following induction, the medium was removed, and the wells were washed once with 200 µl/well PBS. After the wash, 20 µl of a 1:5 dilution (in sterile water) of the stock Cell Culture Lysis Reagent (Luciferase Assay System, Promega Corp., Madison, Wis.) was added to each well, and the plates were incubated for 15 minutes at room temperature. The plates were transferred to a Labsystems Luminoskan microtiter luminometer (Labsystems Inc., Morton Grove, Ill.) which added 40 µl of Luciferase Assay Substrate (Luciferase Assay System, Promega), mixed the reaction for three seconds and integrated the luciferase signal for two seconds per well. The fold induction of luciferase for each agonist was calculated as follows:

$$\text{Fold induction} = \frac{\text{Induced signal} - \text{Uninduced signal}}{\text{Uninduced signal}}$$

Figure 3:
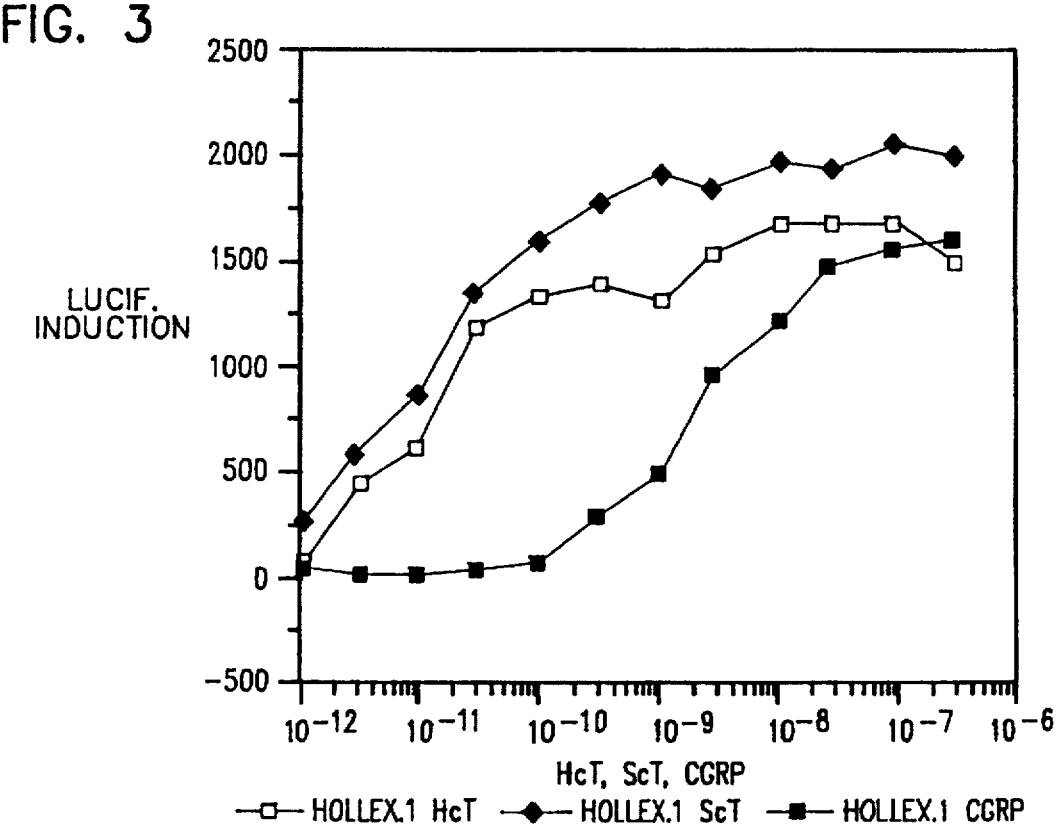
FIG. 3 illustrates the results of a luciferase induction assay for a BHK cell line transfected to express a human calcitonin receptor, where cells were treated with human calcitonin (HcT), salmon calcitonin (ScT) or human CGRP (CGRP)
Figure 4:
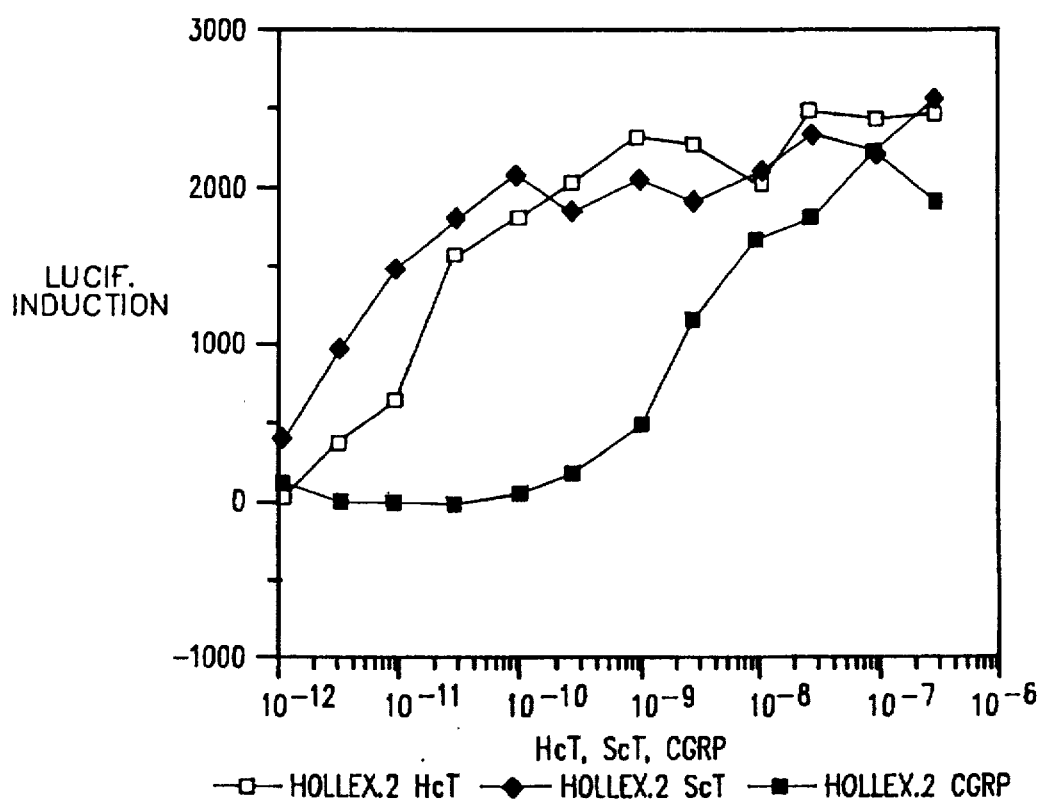
FIG. 4 illustrates the results of a luciferase induction assay for a BHK cell line transfected to express a human calcitonin receptor, where cells were treated with human calcitonin (HcT), salmon calcitonin (ScT) or human CGRP (CGRP).

Hollex1 and Hollex2 showed a 5–10 fold induction of luciferase (FIG. 3 and FIG. 4) for human and salmon calcitonin. The control vector, Zem1698, showed no significant response to any of the agonists mentioned.

The cAMP response of the transfectant clones Hollex1 and Hollex2 to calcitonin and forskolin was also assayed by radioimmunoassay using the cAMP [$^{125}$I] scintillation proximity assay system (Amersham) using the manufacturer's directions. Briefly, either $1\times10^5$ cells per well or $3\times10^5$ cells per well were plated into the wells of a 24-well culture dish and grown for 2 days ($1\times10^5$ cells per well) or overnight ($3\times10^5$ cells per well) in selection medium. Calcitonin and forskolin were prepared in DMEM, 10% fetal calf serum, 10 µM IBMX at 0.0001–1000 nM and 25 µM, respectively.

The growth medium was replaced with 200 µl/well of agonist (either calcitonin or forskolin). The cells were incubated with the agonists for 10 minutes at 37° C. in 5% $CO_2$. Following incubation, 800 µl of boiling water was added to each well. After 15 minutes the supernatants were collected and diluted 1:5 or 1:40 in acetate buffer (cAMP [$^{125}$I] Scintillation Proximity Assay System (Amersham)). Samples were acetylated using triethylamine and acetic anhydride according to the protocol provided by the manufacturer.

A 100 µl aliquot of each acetylated sample was combined with 75 µl of $^{125}$I-cAMP, 75 µl anti-succinyl cAMP antisera and 75 µl of donkey anti-rabbit IgG coupled SPA beads (all assay solutions provided in the cAMP [$^{125}$I] Scintillation Proximity Assay System (Amersham)) in a well of an Dynatech MICROLITE 2 plate. The trays were sealed and incubated overnight with continuous shaking on a rotary platform shaker at 200 rpm. The samples were counted in a Packard Top Count Microplate Scintillation Counter (Packard Instrument Co., Meriden, Conn.). A standard curve of 2–128 fmol acetylated cAMP was also run. Total $^{125}$I-cAMP bound and nonspecific binding were also determined.

Hollex1 showed 12-fold induction of cAMP, Hollex2 showed a 5-fold induction of cAMP levels at saturating Salmon calcitonin concentrations (10–100 nM), and an ED50 of 0.07 nM for Hollex1 and 0.04 nM for Hollex2 using Salmon calcitonin.

E. BINDING AND COMPETITION ASSAYS WITH HOLLEX1 AND HOLLEX2

Clones Hollex1 and Hollex2 were tested for receptor-mediated ability to bind calcitonin using a competition assay. T47D cells were used as a positive control and BHK cells transfected with Zem1698 were used as a negative control.

The cells were plated at a density of $1\times10^5$ cells/well in a 24-well cell culture dish and allowed to grow for 48 hours at 37° C. and 5% $CO_2$ in growth medium (described in previous examples). The cells were rinsed in binding medium (500 ml RPMI 1640 (Sigma, St. Louis, Mo.), 1 mg/ml bacitracin (Sigma), and 1 mg/ml BSA (Boehringer Mannheim)) to remove the serum. Three hundred microliters of binding medium containing radiolabeled $^{125}$I agonist and a serial dilution of unlabeled competitor (Table 1) were added to appropriate wells. The cells were incubated for 1.5 hours at room temperature, and then rinsed 3 times with PBS to remove unincorporated radioactivity. Five hundred microliters of 0.25N NaOH was added to each well to solubilize the cells. The samples were collected from each well and CPMs were counted on a gamma counter.

Data were entered and calculated using Kinetic, EBDA, Ligand, Lowery program from BIOSOFT (Cambridge, U.K.), according to manufacturer's specification. The results of additional experiments are summarized in Table 2.

TABLE 1

Ability of cloned human calcitonin receptor to bind human (A) and salmon (13) calcitonin in competition assays.

A. Human calcitonin concentrations

| $^{125}$I Calcitonin$^a$ | Unlabeled calcitonin | Results (cpms)$^b$ |
|---|---|---|
| $8.7 \times 10^{-3}$ nM | 50 nM | 319 |
| $8.7 \times 10^{-3}$ nM | 30 nM | 533 |
| $8.7 \times 10^{-3}$ nM | 10 nM | 1186 |
| $8.7 \times 10^{-3}$ nM | 3 nM | 2781 |
| $8.7 \times 10^{-3}$ nM | 1 nM | 4657 |
| $8.7 \times 10^{-3}$ nM | 0.3 nM | 5488 |
| $8.7 \times 10^{-3}$ nM | 0.1 nM | 6255 |
| $8.7 \times 10^{-3}$ nM | 0.03 nM | 6518 |
| $8.7 \times 10^{-3}$ nM | 0.01 nM | 6610 |
| $8.7 \times 10^{-3}$ nM | 0.003 nM | 6554 |
| $8.7 \times 10^{-3}$ nM | 0 | 6886 |

B. Salmon calcitonin concentrations

| $^{125}$I Calcitonin$^c$ | Unlabeled calcitonin | Results$^b$ |
|---|---|---|
| $1.7 \times 10^{-2}$ nM | 50 nM | 147 |
| $1.7 \times 10^{-2}$ nM | 30 nM | 458 |
| $1.7 \times 10^{-2}$ nM | 10 nM | 558 |
| $1.7 \times 10^{-2}$ nM | 3 nM | 1639 |
| $1.7 \times 10^{-2}$ nM | 1 nM | 4132 |
| $1.7 \times 10^{-2}$ nM | 0.3 nM | 8421 |
| $1.7 \times 10^{-2}$ nM | 0.1 nM | 9711 |
| $1.7 \times 10^{-2}$ nM | 0.03 nM | 10262 |
| $1.7 \times 10^{-2}$ nM | 0.01 nM | 10278 |
| $1.7 \times 10^{-2}$ nM | 0.003 nM | 10430 |
| $1.7 \times 10^{-2}$ nM | 0 | 10389 |

$^a$Specific activity of $1.9 \times 10^3$ Ci/mM.
$^b$A baseline control of 27 cpm was established using 200 nM unlabeled salmon calcitonin to ensure that all the radiolabeled calcitonin was competed out.
$^c$Specific activity of 945 Ci/mM.

TABLE 2

Summary of binding studies

| | T47D (pos. control) | Hollex1 | Hollex2 |
|---|---|---|---|
| No. receptors/cell | 30–40,000 | 800,000 | 100,000 |
| Kd (nM, avg.) | hCT = 2.1 ± 0.3 | hCT = 4 ± 2.5 | hCT = 1.7 ± 0.1 |
| | sCT = 0.6 ± 0.5 | sCT = 0.5 ± 0.2 | sCT = 0.3 ± 0.01 |

The above results clearly indicate that the human calcitonin receptor clones bind both human and salmon calcitonin, with a greater affinity for human calcitonin compared to the salmon peptide.

F. BINDING AND COMPETITION ASSAYS WITH PLAEX

A pool of transfectants expressing the plaex 1 was tested for receptor-mediated binding to calcitonin using a competition assay. Hollex1 was used as a positive control and BHK cells transfected with Zem228R were used as a negative control.

The cells were plated at a density of $1 \times 10^5$ cells/well in a 24-well cell culture dish and allowed to grow for 48 hours at 37° C. and 5% $CO_2$ in growth medium (described in previous examples). The cells were rinsed in binding medium as described in Example IIIE. Three hundred microliters of hot binding medium containing 10 nM hCT and 5 µCi/ml $^{125}$I hCT. Cold competition was achieved by adding unlabelled hCT to a final concentration of 1 µM were added to appropriate wells. The cells were incubated 1.5 hours at room temperature. Unincorporated radioactivity was removed by three washes with PBS. Five hundred microliters of 1N NaOH was added to each well to solubilize the cells. Each sample was counted on a gamma counter. The data are presented in Table 3.

TABLE 3

| cell line | hot (cpm) | hot/cold (cpm) |
|---|---|---|
| plaex1 | 80,000 | 38,000 |
| Hollex1 | 96,000 | 23,000 |
| BHK/Zem228R | 147 | 105 |

The above results clearly indicate that the BHK transfectants that express the human placental subtype calcitonin receptor binds human calcitonin.

G. INOSITOL TRIPHOSPHATE ASSAY

BHK 570 cells expressing the calcitonin receptor from pHollex or mock-transfected BHK 570 cells were plated into 24-well tissue culture dishes at about 200,000 cells per well. After 24 hours, the cells in each well were labeled by incubation in 0.5 ml of Dulbecco's Modified Eagles Medium (DMEM, JRH Biosciences, Lenexa, Kans.) containing 10% fetal calf serum and 4.0 µCi/ml of myo-(2-$^3$H) inositol (specific activity=20 Ci/mmol; Amersham). At the end of a 24 hour incubation, the cells were washed with 1 ml prewarmed DMEM that had been buffered with 20 mM Hepes, pH 7.0 (Sigma Chemical Co.) containing 10 mM LiCl. The wash medium was removed by aspiration and replaced with 900 µl of fresh buffered medium. The cells were incubated for five to fifteen minutes at 37° C. After incubation, appropriate concentration of each agonist or antagonist was added to triplicate wells, and the cells were incubated for 30 minutes at 37° C.

The reaction was terminated by placing the cells on ice. Following aspiration of the media, the cells were then lysed by the addition of 1 ml of cold DMEM and 1 ml of ice-cold 10% perchloric acid. After ten minutes the cell lysates were transferred to tubes containing 500 µl of 10 mM EDTA, pH 7.0. The samples were neutralized by the addition of 900 µl of 1.5M KOH in 60 mM Hepes buffer and dropwise addition of the KOH-Hepes solution until a pH between 7 and 7.5 was reached. The neutralized samples were frozen at –20° C. overnight. The frozen samples were thawed, and the precipitate was allowed to settle out of the samples. The supernatants were applied to AMPREP minicolumns that had been sequentially washed with 5 ml each of methanol and 1M $KHCO_3$ followed by a wash with 15 ml of water. After the samples were applied, the flow-through was collected. The column was washed with 1 ml of water four times and 1 ml samples were collected after each wash. The inositol phosphates were eluted from the column by four successive 1 ml applications of 0.25M $KHCO_3$ with 1 ml samples collected after each application. Ten milliliters of OPTIFLUOR (Packard Instrument Co., Menden, Conn.) were added to each sample, and the samples were counted. Stimulation of the inositol phosphate pathway was indicated by an increase in labeled inositol phosphate levels. The $ED_{50}$ for human calcitonin in Hollex1 was 6 nM and for salmon calcitonin was 9.5 nM. Hollex2 showed no response.

H. CALCIUM ANALYSIS

Intracellular calcium responses of Hollex1 to calcitonin were assayed essentially as described by Grynkiewicz et al. (*J. Biol. Chem.* 260:3440–3450, 1985, incorporated herein by reference). Transfectants were seeded into 2 well coverglass chambers (NUNC.) at $5 \times 10^4$ cells per chamber. The cells were grown for between one and three days under normal culture conditions in G 418 and methotrexate selection medium. The medium was removed by aspiration, and the chambers were rinsed twice with 1 ml Imaging Buffer (140 mM NaCl 10 mM HEPES, 5.6 mM glucose, 5 mM KCl, 1 mM $CaCl_2$).

After the final rinse 0.5 ml of Fura-2 AM Solution (50 mg fura-2 AM (Molecular Probes, Inc., Eugene, Oreg.), 50 ml DMSO, 5 ml Imaging Buffer), the cells were incubated for 30 minutes in the dark at room temperature. After incubation, the Fura-2 AM Solution was removed and the cells rinsed three times with 1 ml Imaging Buffer. After the final rinse, 0.5 ml of buffer was left in each chamber. The cells were held in the dark at room temperature from 30 to 120 minutes. Imaging was performed on a Nikon Diaphot inverted fluorescence microscope equipped with a mercury arc lamp and 10× and 40× Nikon Fluor dry objective lenses. Experiments were controlled and analyzed using a Sun Microsystems (Mountain View, Calif.) SPARC II workstation and Inovision (Research Triangle Park, N.C.) RATIOTOOL software. Alternate excitation wavelengths were controlled by this software through an automated filter wheel containing 340 nm and 380 nm band pass filters. Emission images were directed by a dichroic mirror (380 nm cutoff) to a Dage-MTI 72 CCD camera equipped with a Genesis II image intensifier and digitally recorded. Results showed that 30–70% of Hollex1 cells had a calcium response to calcitonin. Fewer Hollex2 cells showed a response (1–5%).

The plasmid pHOLLEX was deposited as an *E. coli* XL-1 blue transformant with the American Type Culture Collection, 12301 Parklawn Drive, Rockville, Md. on Sep. 1, 1992 as Accession No. 69067.

EXAMPLE III

BHK cells expressing the cloned calcitonin receptor were assayed to determine their response to extracellular calcium. Cells were washed three times with a buffer (140 mM NaCl, 5 mM KCl, 0.5 mM $MgCl_2$, 0.5 mM $CaCl_2$ (concentration varied in some experiments), 10 mM glucose, 10 mM HEPES, pH 7.4) made using high purity salts (Aldrich, Milwaukee, Wis.) and sterile water (Baxter, McGaw Park, Ill.). Cells were loaded with fura-2 AM (Molecular Probes Inc.) (10 μg/ml) for 30 minutes essentially as described above, then washed an additional three times. Slides were mounted at room temperature on an inverted microscope (EPIPHOT, Nikon), and a field of cells (typically 20–30 cells) was located using a 40× Nikon fluor objective. The ratio of fura-2 emission at excitation wavelengths of 340 and 380 nm was recorded every 5 seconds. Individual cells were analyzed on a computer workstation (Sun Microsystems) using a software system designed for ratio imaging (Inovision). The concentration of calcium chloride in buffers was determined by comparison to calcium standards on a calcium analyzer (Nova Biomedical Corp. Waltham, Mass.). All experiments were reproduced three to eight times. Fura-2 ratio 340 nm to 380 nm values (R) were converted to $[Ca^{2+}]_i$ concentrations after calibration of the instrument using the formula:calcium (nm)=2240[R-0.3)/(20-R)]. Basal $[Ca^{2+}]_i$ concentrations were typically 80–150 nm. The peak fura-2 ratios 340/380 of individual cells exposed to 20 nm salmon calcitonin followed by 25 mM calcium chloride were averaged for some experiments and converted to $[Ca^{2+}]_i$ concentrations. Standard error was calculated at a 99% level using a Z score of 2.58 (n>30).

A transfected BHK cell line expressing about 700,000 calcitonin receptors/cell showed maximal transient $[Ca^{2+}]_i$ increases with 10–20 nm salmon or human calcitonin. Application of 25 mM extracellular calcium chloride to the same cells (following a five-minute period of darkness to reduce the total exposure of cells to UV light) with or without calcitonin pretreatment produced a rapid and sustained increase in $[Ca^{2+}]_i$. The magnitude of the latter response was comparable to that induced by calcitonin and was not significantly altered (p<0.01) by calcitonin pretreatment. The response to 25 mM extracellular calcium chloride returned to an elevated basal level in about 20 minutes. Addition of 25 mM extracellular calcium for two minutes followed by a continuous wash with cell buffer resulted in a rapid and transient increase in $[Ca^{2+}]_i$. Addition of 73 mM KCl instead of $CaCl_2$ had no effect.

Transfected BHK cell lines expressing human calcitonin receptor levels of 100,000 and 150,000 receptors/cell were also assayed. Both cell lines responded to calcitonin and extracellular calcium with increases in $[Ca^{2+}]_i$. These cells showed a marked potentiation of the response to extracellular calcium by calcitonin pretreatment. Control BHK cell lines showed no response to extracellular calcium.

The peak $[Ca^{2+}]_i$ of single cells in response to both calcitonin and extracellular calcium was averaged (±S.E. at p<0.01) for each cell line expressing the calcitonin receptor. The average peak responses were proportional to the average number of receptors per cell expressed by a given cell line.

The dose response to extracellular calcium was characterized in the cell line expressing 700,000 receptors/cell. A significant response was observed with as little as a 2 mM increase in extracellular calcium over basal (1.3 mM), and maximum response occurred at approximately 14 mM. The effective concentration for half-maximal response was 8–10 mM as determined from an apparently linear double reciprocal plot of extracellular calcium concentration vs. area of response under each curve. These dose-response concentrations of extracellular calcium are similar to those reported to induce elevated $[Ca^{2+}]_i$ in isolated osteoclasts.

It is evident from the above results that the subject invention provides cloned human calcitonin receptors and cells which express the cloned receptors. The vectors containing the cloned sequences and cells which express them find use in, inter alia, methods for screening and identifying agonists useful in treating and preventing osteoporosis and other diseases characterized by abnormal bone resorption. Furthermore, the invention provides economical methods to prepare human calcitonin receptors, conveniently from large scale expression systems.

All publications and patent applications mentioned in this specification are indicative of the level of skill of those skilled in the art to which this invention pertains. All publications, patents and patent applications are herein incorporated by reference to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for identifying a compound which alters human calcitonin receptor mediated metabolism in a cell, which comprises:

incubating the compound with eukaryotic cells transformed or transfected with a DNA sequence which directs expression of (a) a human calcitonin receptor polypeptide having the amino acid sequence shown in SEQ ID NO: 2, (b) a human calicitonin receptor polypeptide having the amino acid sequence shown in SEQ ID NO: 25, (c) a naturally occurring allelic variant of (a) or (b), or (d) a polypeptide comprising a N-terminal ligand-binding domain, a first transmembrane domain, and a first intracellular domain of (a), (b), or (c), monitoring the metabolism of the cells, and determining the effect of said compound on receptor-mediated metabolism in the cells.

2. The method of claim 1, wherein the compound is incubated with the cells in the presence of human or salmon calcitonin.

3. The method of claim 1, wherein the metabolism which is monitored in the eukaryotic cell is inositol phosphate metabolism.

4. A method according to claim 1, wherein the DNA sequence comprising SEQ ID NO: 1.

5. A method according to claim 1, wherein the DNA sequence comprising SEQ ID NO: 24.

6. A method according to claim 1, wherein the transformed or transfected cells express a human calcitonin receptor polypeptide having the amino acid sequence shown in SEQ ID NO: 2.

7. A method according to claim 1, wherein the transformed or transfected cells express a human calcitonin receptor polypeptide having the amino acid sequence shown in SEQ ID NO: 25.

8. A method according to claim 1, wherein the cells do not express substantial amounts of endogenous calcitonin receptor.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 3012 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: pHOLLEX ( i x ) FEATURE:
( A ) NAME/KEY: CDS
( B ) LOCATION: 52..1476

( x i ) SEQUENCE DESCRIPTION: SEQ ID NO:1:

```
GAATTCGCGG CCGCCAGAAT TCCAGGACAA AGAGATCTTC AAAAATCAAA A ATG AGG         57
                                                           Met Arg
                                                           1

TTC ACA TTT ACA AGC CGG TGC TTG GCA CTG TTT CTT CTT CTA AAT CAC        105
Phe Thr Phe Thr Ser Arg Cys Leu Ala Leu Phe Leu Leu Leu Asn His
        5                   10                  15

CCA ACC CCA ATT CTT CCT GCC TTT TCA AAT CAA ACC TAT CCA ACA ATA        153
Pro Thr Pro Ile Leu Pro Ala Phe Ser Asn Gln Thr Tyr Pro Thr Ile
        20                  25                  30

GAG CCC AAG CCA TTT CTT TAC GTC GTA GGA CGA AAG AAG ATG ATG GAT        201
Glu Pro Lys Pro Phe Leu Tyr Val Val Gly Arg Lys Lys Met Met Asp
35                  40                  45                      50

GCA CAG TAC AAA TGC TAT GAC CGA ATG CAG CAG TTA CCC GCA TAC CAA        249
Ala Gln Tyr Lys Cys Tyr Asp Arg Met Gln Gln Leu Pro Ala Tyr Gln
                    55                  60                  65

GGA GAA GGT CCA TAT TGC AAT CGC ACC TGG GAT GGA TGG CTG TGC TGG        297
Gly Glu Gly Pro Tyr Cys Asn Arg Thr Trp Asp Gly Trp Leu Cys Trp
                70                  75                  80

GAT GAC ACA CCG GCT GGA GTA TTG TCC TAT CAG TTC TGC CCA GAT TAT        345
Asp Asp Thr Pro Ala Gly Val Leu Ser Tyr Gln Phe Cys Pro Asp Tyr
        85                  90                  95

TTT CCG GAT TTT GAT CCA TCA GAA AAG GTT ACA AAA TAC TGT GAT GAA        393
Phe Pro Asp Phe Asp Pro Ser Glu Lys Val Thr Lys Tyr Cys Asp Glu
        100                 105                 110

AAA GGT GTT TGG TTT AAA CAT CCT GAA AAC AAT CGA ACC TGG TCC AAC        441
Lys Gly Val Trp Phe Lys His Pro Glu Asn Asn Arg Thr Trp Ser Asn
115                 120                 125                     130

TAT ACT ATG TGC AAT GCT TTC ACT CCT GAG AAA CTG AAG AAT GCA TAT        489
Tyr Thr Met Cys Asn Ala Phe Thr Pro Glu Lys Leu Lys Asn Ala Tyr
                    135                 140                 145

GTT CTG TAC TAT TTG GCT ATT GTG GGT CAT TCT TTG TCA ATT TTC ACC        537
Val Leu Tyr Tyr Leu Ala Ile Val Gly His Ser Leu Ser Ile Phe Thr
                150                 155                 160

CTA GTG ATT TCC CTG GGG ATT TTC GTG TTT TTC AGG AGC CTT GGC TGC        585
Leu Val Ile Ser Leu Gly Ile Phe Val Phe Phe Arg Ser Leu Gly Cys
        165                 170                 175

CAA AGG GTA ACC CTG CAC AAG AAC ATG TTT CTT ACT TAC ATT CTG AAT        633
Gln Arg Val Thr Leu His Lys Asn Met Phe Leu Thr Tyr Ile Leu Asn
        180                 185                 190

TCT ATG ATT ATC ATC ATC CAC CTG GTT GAA GTA GTA CCC AAT GGA GAG        681
```

```
Ser Met Ile Ile Ile Ile His Leu Val Glu Val Val Pro Asn Gly Glu
195                 200                 205                 210

CTC GTG CGA AGG GAC CCG GTG AGC TGC AAG ATT TTG CAT TTT TTC CAC    729
Leu Val Arg Arg Asp Pro Val Ser Cys Lys Ile Leu His Phe Phe His
            215                 220                 225

CAG TAC ATG ATG GCC TGC AAC TAT TTC TGG ATG CTC TGT GAA GGG ATC    777
Gln Tyr Met Met Ala Cys Asn Tyr Phe Trp Met Leu Cys Glu Gly Ile
                230                 235                 240

TAT CTT CAT ACA CTC ATT GTC GTG GCT GTG TTT ACT GAG AAG CAA CGC    825
Tyr Leu His Thr Leu Ile Val Val Ala Val Phe Thr Glu Lys Gln Arg
            245                 250                 255

TTG CGG TGG TAT TAT CTC TTG GGC TGG GGG TTC CCG CTG GTG CCA ACC    873
Leu Arg Trp Tyr Tyr Leu Leu Gly Trp Gly Phe Pro Leu Val Pro Thr
    260                 265                 270

ACT ATC CAT GCT ATT ACC AGG GCC GTG TAC TTC AAT GAC AAC TGC TGG    921
Thr Ile His Ala Ile Thr Arg Ala Val Tyr Phe Asn Asp Asn Cys Trp
275                 280                 285                 290

CTG AGT GTG GAA ACC CAT TTG CTT TAC ATA ATC CAT GGA CCT GTC ATG    969
Leu Ser Val Glu Thr His Leu Leu Tyr Ile Ile His Gly Pro Val Met
                295                 300                 305

GCG GCA CTT GTG GTC AAT TTC TTC TTT TTG CTC AAC ATT GTC CGG GTG    1017
Ala Ala Leu Val Val Asn Phe Phe Phe Leu Leu Asn Ile Val Arg Val
            310                 315                 320

CTT GTG ACC AAA ATG AGG GAA ACC CAT GAG GCG GAA TCC CAC ATG TAC    1065
Leu Val Thr Lys Met Arg Glu Thr His Glu Ala Glu Ser His Met Tyr
        325                 330                 335

CTG AAG GCT GTG AAG GCC ACC ATG ATC CTT GTG CCC CTG CTG GGA ATC    1113
Leu Lys Ala Val Lys Ala Thr Met Ile Leu Val Pro Leu Leu Gly Ile
    340                 345                 350

CAG TTT GTC GTC TTT CCC TGG AGA CCT TCC AAC AAG ATG CTT GGG AAG    1161
Gln Phe Val Val Phe Pro Trp Arg Pro Ser Asn Lys Met Leu Gly Lys
355                 360                 365                 370

ATA TAT GAT TAC GTG ATG CAC TCT CTG ATT CAT TTC CAG GGC TTC TTT    1209
Ile Tyr Asp Tyr Val Met His Ser Leu Ile His Phe Gln Gly Phe Phe
                375                 380                 385

GTT GCG ACC ATC TAC TGC TTC TGC AAC AAT GAG GTC CAA ACC ACC GTG    1257
Val Ala Thr Ile Tyr Cys Phe Cys Asn Asn Glu Val Gln Thr Thr Val
            390                 395                 400

AAG CGC CAA TGG GCC CAA TTC AAA ATT CAG TGG AAC CAG CGT TGG GGG    1305
Lys Arg Gln Trp Ala Gln Phe Lys Ile Gln Trp Asn Gln Arg Trp Gly
        405                 410                 415

AGG CGC CCC TCC AAC CGC TCT GCT CGC GCT GCA GCC GCT GCT GCG GAG    1353
Arg Arg Pro Ser Asn Arg Ser Ala Arg Ala Ala Ala Ala Ala Ala Glu
    420                 425                 430

GCT GGC GAC ATC CCA ATT TAC ATC TGC CAT CAG GAG CTG AGG AAT GAA    1401
Ala Gly Asp Ile Pro Ile Tyr Ile Cys His Gln Glu Leu Arg Asn Glu
435                 440                 445                 450

CCA GCC AAC AAC CAA GGC GAG GAG AGT GCT GAG ATC ATC CCT TTG AAT    1449
Pro Ala Asn Asn Gln Gly Glu Glu Ser Ala Glu Ile Ile Pro Leu Asn
                455                 460                 465

ATC ATA GAG CAA GAG TCA TCT GCT TGAATGTAAG GCAAACACAG CATCGTGATC    1503
Ile Ile Glu Gln Glu Ser Ser Ala
            470                 475

ACTGAGCCAT CATTTCCTGG GAGAAAGACC ATGCATTTAA AGTATTCTCC ATCCTCCAG    1563

GAACCGAACA TATCATTTGT GAAGAATTAT TCAGTGAATT TGTCCATTGT AAATCTGAAG    1623

AAAGTTATTC TTGGTACTGT TGCTTTGGGA GACAGTCTAG GAATGGAGTC TCCCACTGCA    1683

ACTTGTGAAC TCCATCATTC ATCCAGGACT GAGATGCAAA TGTCACAGTA ATGCAAGCAA    1743

AGTATCAAAG AAAAACAATG AAATTGACCT AGTTCAGATA CAGGGTGCTC CTTGTCAATA    1803
```

-continued

```
CTGAGCCATT TATACCTTTG AAATATTAAA ATCACTGTCA ATATTTTTAT TTTTAACTCT    1863
GGATTTTGAA TTAGATTATT TCTGTATTTG GCTATGGATC TGATTTTTAA TTTTTTTAAA    1923
TTTCAGTCAA TTCTGATGTT ACTGAGATGT TTTACCATCC TTACAATGTA AACCACATGA    1983
ACTACGTGAC CTCTGCAAGA CAAAGCGGCT TTCTAATAGA GAGATTAGTA AATATGTGAA    2043
GAAAAAGACC TGCATTGGC  AGAAGATGTA TGCTTGAAT  GCAAAAGAAA TTTAGAGTCA    2103
ATTTGCTGAA AACATTACAT GCTCAGCTTG GTTTTGGACA AGCCTGTCCA TTGGGCAGGA    2163
CCTAGCTGTT GTAAAGAATT GGTCTTAATG TTGAATGTAT TTTGGTTGCT GATGTTTATA    2223
AACTGAGAGG TCACAAAGAA TCTATCACTA AAAATTTTTA CAAAACTGCC AAAAATATAA    2283
TTCTTAGTGG AAGACAATAC TCCCTTTAAA GAGAGTTTGC CACTCCCCTA AACTCCAGGA    2343
TTTATAAAGC AAATTACTCC AAGGTTTATA AAGCAGATTA CCTCTTGCCC TTGGGTGCTA    2403
TCTAGCAGTA AAAGATAAAT TTGTTGAATA TTGGTAATTA AAAGACTCCA CATAAGTCCA    2463
TTAACTGCTT TCCACCCAGC TTCAAAGTCC AAAAAGAGCT CAGGCTTTTC CAGGAAGATC    2523
CAGGAGGGCT AATTAGAAAT CAACTTGTGG TTGACCGCTT GTTTCTTGTT ATTACCAAAC    2583
AGGAGGGGAA AAAATTAACT GCTCCAAATT TAACCATAAA TCAATTCATG TTTAACGTTT    2643
CTCATTAAAA TCCAGTATTA TATTATCATA TCTCTCTTTA CTTCCCAGTA TAAGATTTTT    2703
GAAAATCCTG AATAAACCAG TATCGTTACT GGCACCTGAA ATTAATTTGT GAATTTGCAA    2763
CAGTAATCAG AGTTACCATT ATTTAATTTG TATGCTAAAT GAGGAGGTAC ATTGAAACCC    2823
TCCAAATCTC CAGTCTCATC TATGTCATAT TTTGCCACTG CCTTTCAGAA GTGATTTAGT    2883
TGTGGAAAGA TAATAAATTG ATTTGTTATG GTTACATATT TAGCGCACCC AGAGAAAATT    2943
AATTATATTT CTACAGAGAA AATGAATTTG GGATACTAAA GTAGTTTAAG TCTCCTTTAC    3003
TGAATGAAA                                                           3012
```

( 2 ) INFORMATION FOR SEQ ID NO:2:

( i ) SEQUENCE CHARACTERISTICS:
( A ) LENGTH: 474 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Arg Phe Thr Phe Thr Ser Arg Cys Leu Ala Leu Phe Leu Leu Leu
 1               5                  10                  15

Asn His Pro Thr Pro Ile Leu Pro Ala Phe Ser Asn Gln Thr Tyr Pro
                20                  25                  30

Thr Ile Glu Pro Lys Pro Phe Leu Tyr Val Val Gly Arg Lys Lys Met
            35                  40                  45

Met Asp Ala Gln Tyr Lys Cys Tyr Asp Arg Met Gln Gln Leu Pro Ala
        50                  55                  60

Tyr Gln Gly Glu Gly Pro Tyr Cys Asn Arg Thr Trp Asp Gly Trp Leu
 65                 70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
               100                 105                 110

Asp Glu Lys Gly Val Trp Phe Lys His Pro Glu Asn Asn Arg Thr Trp
           115                 120                 125

Ser Asn Tyr Thr Met Cys Asn Ala Phe Thr Pro Glu Lys Leu Lys Asn
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     |     | 130 |     |     |     |     | 135 |     |     |     | 140 |     |     |
| Ala<br>145 | Tyr | Val | Leu | Tyr | Tyr<br>150 | Leu | Ala | Ile | Val | Gly<br>155 | His | Ser | Leu | Ser | Ile<br>160 |
| Phe | Thr | Leu | Val | Ile<br>165 | Ser | Leu | Gly | Ile | Phe<br>170 | Val | Phe | Phe | Arg | Ser<br>175 | Leu |
| Gly | Cys | Gln | Arg<br>180 | Val | Thr | Leu | His | Lys<br>185 | Asn | Met | Phe | Leu | Thr<br>190 | Tyr | Ile |
| Leu | Asn | Ser<br>195 | Met | Ile | Ile | Ile | His<br>200 | Leu | Val | Glu | Val<br>205 | Val | Pro | Asn |
| Gly | Glu<br>210 | Leu | Val | Arg | Arg | Asp<br>215 | Pro | Val | Ser | Cys | Lys<br>220 | Ile | Leu | His | Phe |
| Phe<br>225 | His | Gln | Tyr | Met | Met<br>230 | Ala | Cys | Asn | Tyr | Phe<br>235 | Trp | Met | Leu | Cys | Glu<br>240 |
| Gly | Ile | Tyr | Leu | His<br>245 | Thr | Leu | Ile | Val | Val<br>250 | Ala | Val | Phe | Thr | Glu<br>255 | Lys |
| Gln | Arg | Leu | Arg<br>260 | Trp | Tyr | Tyr | Leu | Leu<br>265 | Gly | Trp | Gly | Phe | Pro<br>270 | Leu | Val |
| Pro | Thr | Thr<br>275 | Ile | His | Ala | Ile | Thr<br>280 | Arg | Ala | Val | Tyr | Phe<br>285 | Asn | Asp | Asn |
| Cys | Trp<br>290 | Leu | Ser | Val | Glu | Thr<br>295 | His | Leu | Leu | Tyr | Ile<br>300 | Ile | His | Gly | Pro |
| Val<br>305 | Met | Ala | Ala | Leu | Val<br>310 | Val | Asn | Phe | Phe | Phe<br>315 | Leu | Leu | Asn | Ile | Val<br>320 |
| Arg | Val | Leu | Val | Thr<br>325 | Lys | Met | Arg | Glu | Thr<br>330 | His | Glu | Ala | Glu | Ser<br>335 | His |
| Met | Tyr | Leu | Lys<br>340 | Ala | Val | Lys | Ala | Thr<br>345 | Met | Ile | Leu | Val | Pro<br>350 | Leu | Leu |
| Gly | Ile | Gln<br>355 | Phe | Val | Val | Phe | Pro<br>360 | Trp | Arg | Pro | Ser | Asn<br>365 | Lys | Met | Leu |
| Gly | Lys<br>370 | Ile | Tyr | Asp | Tyr | Val<br>375 | Met | His | Ser | Leu | Ile<br>380 | His | Phe | Gln | Gly |
| Phe<br>385 | Phe | Val | Ala | Thr | Ile<br>390 | Tyr | Cys | Phe | Cys | Asn<br>395 | Asn | Glu | Val | Gln | Thr<br>400 |
| Thr | Val | Lys | Arg | Gln<br>405 | Trp | Ala | Gln | Phe | Lys<br>410 | Ile | Gln | Trp | Asn | Gln<br>415 | Arg |
| Trp | Gly | Arg | Arg<br>420 | Pro | Ser | Asn | Arg | Ser<br>425 | Ala | Arg | Ala | Ala | Ala<br>430 | Ala |
| Ala | Glu | Ala<br>435 | Gly | Asp | Ile | Pro | Ile<br>440 | Tyr | Ile | Cys | His | Gln<br>445 | Glu | Leu | Arg |
| Asn | Glu<br>450 | Pro | Ala | Asn | Asn | Gln<br>455 | Gly | Glu | Glu | Ser | Ala<br>460 | Glu | Ile | Ile | Pro |
| Leu<br>465 | Asn | Ile | Ile | Glu | Gln<br>470 | Glu | Ser | Ser | Ala |     |     |     |     |     |     |

( 2 ) INFORMATION FOR SEQ ID NO:3:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC982

( x i ) SEQUENCE DESCRIPTION: SEQ ID NO:3:

```
AATTCCCCTC CCGCGAAGGC GTCGGCGCGG GGCTGGCGTA GGGCCTGCGT CAGCTGCAGC          60
```

CCGCCGGAGC T                                                                                            71

( 2 ) INFORMATION FOR SEQ ID NO:4:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC983

( x i ) SEQUENCE DESCRIPTION: SEQ ID NO:4:

CCGGCGGGCT GCAGCTGACG CAGGCCCTAC GCCAGCCCCG CGCCGACGCC TTCGCGGGAG      60
GGG                                                                    63

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1773

( x i ) SEQUENCE DESCRIPTION: SEQ ID NO:5:

AATTAGGGAG ACCGGAATTC TGTGCTCTGT CAA                                   33

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1774

( x i ) SEQUENCE DESCRIPTION: SEQ ID NO:6:

AATTTTGACA GAGCACAGAA TTCCGGTCTC CCT                                   33

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3509

( x i ) SEQUENCE DESCRIPTION: SEQ ID NO:7:

CAAATTGACG TCATGGTAAA AATTGACGTC ATGGTAAG                              38

( 2 ) INFORMATION FOR SEQ ID NO:8:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3510

( x i ) SEQUENCE DESCRIPTION: SEQ ID NO:8:

AATTCTTACC ATGACGTCAA TTTTTACCAT GACGTCAATT TGAGCT        46

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4418

( x i ) SEQUENCE DESCRIPTION: SEQ ID NO:9:

TTAATTAAGG ACTCTCCTGC AGTGGATGCC TTAATTAATG CA        42

( 2 ) INFORMATION FOR SEQ ID NO:10:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4419

( x i ) SEQUENCE DESCRIPTION: SEQ ID NO:10:

TTAATTAAGG CATCCACTGC AGGAGAGTCC TTAATTAATG CA        42

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4698

( x i ) SEQUENCE DESCRIPTION: SEQ ID NO:11:

ACTCTCCGGT TRCARAARCA RTADAT        26

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4699

( x i ) SEQUENCE DESCRIPTION: SEQ ID NO:12:

CATCCACGGC AYAARAAYAT GTTYYT        26

( 2 ) INFORMATION FOR SEQ ID NO:13:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3168

( x i ) SEQUENCE DESCRIPTION: SEQ ID NO:13:

AATTGAGCTC G                                                                                               11

( 2 ) INFORMATION FOR SEQ ID NO:14:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3169

( x i ) SEQUENCE DESCRIPTION: SEQ ID NO:14:

AATTCGAGCT C                                                                                               11

( 2 ) INFORMATION FOR SEQ ID NO:15:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC2938

( x i ) SEQUENCE DESCRIPTION: SEQ ID NO:15:

GACAGAGCAC AGAATTCACT AGTGAGCTCT TTTTTTTTT TTTT                                                             44

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5471

( x i ) SEQUENCE DESCRIPTION: SEQ ID NO:16:

TACCCGCATA CCAAGGAGAA G                                                                                    21

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5468

( x i ) SEQUENCE DESCRIPTION: SEQ ID NO:17:

AAGAGATAAT ACCACCGCAA GC                                                                                   22

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5469

( x i ) SEQUENCE DESCRIPTION: SEQ ID NO:18:

CCATCAGAAA AGGTTACAAA AT 22

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5474

( x i ) SEQUENCE DESCRIPTION: SEQ ID NO:19:

CACAGAGCAT CCAGAAATAG TT 22

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5993

( x i ) SEQUENCE DESCRIPTION: SEQ ID NO:20:

CAGCCAAGGC TCAATGCCTT CCTGAAAAAC ACGAA 35

( 2 ) INFORMATION FOR SEQ ID NO:21:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5162

( x i ) SEQUENCE DESCRIPTION: SEQ ID NO:21:

AATTCTATGA TTATCATCAT CCACCTGGTT GAAGTAGTAC CCAATGGAGA CCT 53

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5470

( x i ) SEQUENCE DESCRIPTION: SEQ ID NO:22:

TTGCGGTGGT ATTATCTCTT G 21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC5465

( x i ) SEQUENCE DESCRIPTION: SEQ ID NO:23:

TGTTGGCTGG TTCATTCCTC A                                                                          21

( 2 ) INFORMATION FOR SEQ ID NO:24:

( i ) SEQUENCE CHARACTERISTICS:
        ( A ) LENGTH: 3416 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: pOvex ( i x ) FEATURE:
        ( A ) NAME/KEY: CDS
        ( B ) LOCATION: 52..594

( x i ) SEQUENCE DESCRIPTION: SEQ ID NO:24:

```
GAATTCGCGG CCGCCAGAAT TCCAGGACAA AGAGATCTTC AAAAATCAAA A ATG AGG         57
                                                          Met Arg
                                                            1

TTC ACA TTT ACA AGC CGG TGC TTG GCA CTG TTT CTT CTT CTA AAT CAC         105
Phe Thr Phe Thr Ser Arg Cys Leu Ala Leu Phe Leu Leu Leu Asn His
          5                  10                  15

CCA ACC CCA ATT CTT CCT GCC TTT TCA AAT CAA ACC TAT CCA ACA ATA         153
Pro Thr Pro Ile Leu Pro Ala Phe Ser Asn Gln Thr Tyr Pro Thr Ile
         20                  25                  30

GAG CCC AAG CCA TTT CTT TAC GTC GTA GGA CGA AAG AAG ATG ATG GAT         201
Glu Pro Lys Pro Phe Leu Tyr Val Val Gly Arg Lys Lys Met Met Asp
 35                  40                  45                  50

GCA CAG TAC AAA TGC TAT GAC CGA ATG CAG CAG TTA CCC GCA TAC CAA         249
Ala Gln Tyr Lys Cys Tyr Asp Arg Met Gln Gln Leu Pro Ala Tyr Gln
                 55                  60                  65

GGA GAA GGT CCA TAT TGC AAT CGC ACC TGG GAT GGA TGG CTG TGC TGG         297
Gly Glu Gly Pro Tyr Cys Asn Arg Thr Trp Asp Gly Trp Leu Cys Trp
         70                  75                  80

GAT GAC ACA CCG GCT GGA GTA TTG TCC TAT CAG TTC TGC CCA GAT TAT         345
Asp Asp Thr Pro Ala Gly Val Leu Ser Tyr Gln Phe Cys Pro Asp Tyr
         85                  90                  95

TTT CCG GAT TTT GAT CCA TCA GAA AAG GTT ACA AAA TAC TGT GAT GAA         393
Phe Pro Asp Phe Asp Pro Ser Glu Lys Val Thr Lys Tyr Cys Asp Glu
100                 105                 110

AAA GGT GTT TGG TTT AAA CAT CCT GAA AAC AAT CGA ACC TGG TCC AAC         441
Lys Gly Val Trp Phe Lys His Pro Glu Asn Asn Arg Thr Trp Ser Asn
115                 120                 125                 130

TAT ACT ATG TGC AAT GCT TTC ACT CCT GAG AAA CTG AAG AAT GCA TAT         489
Tyr Thr Met Cys Asn Ala Phe Thr Pro Glu Lys Leu Lys Asn Ala Tyr
                135                 140                 145

GTT CTG TAC TAT TTG GCT ATT GTG GGT CAT TCT TTG TCA ATT TTC ACC         537
Val Leu Tyr Tyr Leu Ala Ile Val Gly His Ser Leu Ser Ile Phe Thr
        150                 155                 160

CTA GTG ATT TCC CTG GGG ATT TTC GTG TTT TTC AGT TCT CAT GTT TAT         585
Leu Val Ile Ser Leu Gly Ile Phe Val Phe Phe Ser Ser His Val Tyr
        165                 170                 175

CAT GAA TAACACGTGA TCCTAGGAGC CTTGGCTGCC AAAGGGTAAC CCTGCACAAG          641
His Glu
    180

AACATGTTTC TTACTTACAT TCTGAATTCT ATGATTATCA TCATCCACCT GGTTGAAGTA       701

GTACCCAATG GAGAGCTCGT GCGAAGGGAC CCGGTGAGCT GCAAGATTTT GCATTTTTC        761
```

```
CACCAGTACA TGATGGCCTG CAACTATTTC TGGATGCTCT GTGAAGGGAT CTATCTTCAT    821
ACACTCATTG TCGTGGCTGT GTTACTGAG  AAGCAACGCT TGCGGTGGTA TTATCTCTTG    881
GGCTGGGGGT TCCCGCTGGT GCCAACCACT ATCCATGCTA TTACCAGGGC CGTGTACTTC    941
AATGACAACT GCTGGCTGAG TGTGGAAACC CATTTGCTTT ACATAATCCA TGGACCTGTC   1001
ATGGCGGCAC TTGTGGTCAA TTTCTTCTTT TTGCTCAACA TTGTCCGGGT GCTTGTGACC   1061
AAAATGAGGG AAACCCATGA GGCGGAATCC CACATGTACC TGAAGGCTGT GAAGGCCACC   1121
ATGATCCTTG TGCCCCTGCT GGGAATCCAG TTTGTCGTCT TTCCCTGGAG ACCTTCCAAC   1181
AAGATGCTTG GGAAGATATA TGATTACGTG ATGCACTCTC TGATTCATTT CCAGGGCTTC   1241
TTTGTTGCGA CCATCTACTG CTTCTGCAAC AATGAGGTCC AAACCACCGT GAAGCGCCAA   1301
TGGGCCCAAT TCAAAATTCA GTGGAACCAG CGTTGGGGGA GGCGCCCCTC CAACCGCTCT   1361
GCTCGCGCTG CAGCCGCTGC TGCGGAGGCT GGCGACATCC CAATTTACAT CTGCCATCAG   1421
GAGCTGAGGA ATGAACCAGC CAACAACCAA GGCGAGGAGA GTGCTGAGAT CATCCCTTTG   1481
AATATCATAG AGCAAGAGTC ATCTGCTTGA ATGTGAAGGC AAACACAGCA TCGTGATCAC   1541
TGAGCCATCA TTTCCTGGGA GAAAGACCAT GCATTTAAAG TATTCTCCAT CCTCCCAGGA   1601
ACCGAACATA TCATTTGTGA AGAATTATTC AGTGAATTTG TCCATTGTAA ATCTGAAGAA   1661
AGTTATTCTT GGTACTGTTG CTTTGGGAGA CAGTCTAGGA ATGGAGTCTC CCACTGCAAC   1721
TTGTGAACTC CATCATTCAT CCAGGACTGA GATGCAAATG TCACAGTAAT GCAAGCAAAG   1781
TATCAAAGAA AAACAATGAA ATTGACCTAG TTCAGATACA GGTGCTCCT  TGTCAATACT   1841
GAGCCATTTA TACCTTTGAA ATATTAAAAT CACTGTCAAT ATTTTATTT  TTAACTCTGG   1901
ATTTTGAATT AGATTATTTC TGTATTTGGC TATGGATCTG ATTTTTAATT TTTTTAAATT   1961
TCAGTCAATT CTGATGTTAC TGAGATGTTT TACCATCCTT ACAATGTAAA CCACATGAAC   2021
TACGTGACCT CTGCAAGACA AAGCGGCTTT CTAATAGAGA GATTAGTAAA TATGTGAAGA   2081
AAAAGACCTG CATTTGGCAG GAAGATGTAT GCTTTGAATG CAAAAGAAAT TTAGAGTCAA   2141
TTTGCTGAAA ACATTACATG CTCAGCTTGG TTTTGGACAA GCCTGTCCAT TGGGCAGGAC   2201
CTAGCTGTTG TAAAGAATTG GTCTTAATGT TGAATGTATT TTGGTTGCTG ATGTTTATAA   2261
ACTGAGAGGT CACAAAGAAT CTATCACTAA AAATTTTTAC AAAACTGCCA AAAATATAAT   2321
TCTTAGTGGA AGACAATACT CCCTTTAAAG AGAGTTTGCC ACTCCCCTAA ACTCCAGGAT   2381
TTATAAAGCA AATTACTCCA AGGTTTATAA AGCAGATTAC CTCTTGCCCT TGGGTGCTAT   2441
CTAGCAGTAA AAGATAAATT TGTTGAATAT TGGTAATTAA AAGACTCCAC ATAAGTCCAT   2501
TAACTGCTTT CCACCCAGCT TCAAAGCTTA AAAAGAGCTC AGGCTTTTCC AGGAAGATCC   2561
AGGAGGGCTA ATTAGAAATC AACTTGTGGT TGACCGCTTG TTTCTTGTTA TTACCAAACA   2621
GGAGGGGAAA AAATTAACTG CTCCAAATTT AACCATAAAT CAATTCATGT TTAACGTTTC   2681
TCATTAAAAT CCAGTATTAT ATTATCATAT CTCTCTTTAC TTCCCAGTAT AAGATTTTTG   2741
AAAATCCTGA ATAAACCAGT ATCGTTACTG GCACCTGAAA TTAATTTGTG AATTTGCAAC   2801
AGTAATCAGA GTTACCATTA TTTAATTTGT ATGCTAAATG AGGAGGTACA TTGAAACCCT   2861
CCAAATCTCC AGTCTCATCT ATGTCATATT TTGCCACTGC CTTTCAGAAG TGATTTAGTT   2921
GTGGAAAGAT AATAAATTGA TTTGTTATGG TTACATATTT AGCGCACCCA GAGAAAATTA   2981
ATTATATTTC TACAGAGAAA ATGAATTTGG GATACTAAAG TAGTTTAAGT CTCCTTTACT   3041
GAATGTAAGG GGGGATCGA  AAAGAAGGTA TTTTTCCAAT CACAGTGTTA TGTAGTATTG   3101
TTCTATTTTT GTTTACAAAC ATGGAAAACA GAGTATTTCT GGCAGCTGTG GTACAAATGT   3161
```

```
GATAATATAT TGCTAAAATA TTTTAGATGT TATTATGCTA ATATAGTAGG GGTTGAAGAA      3221

AACAAAATAG CTTATTATAG AATTGCACAT AGTTCTGCCC AAATTATGTG AAATGCTTAT      3281

GCTTGTGTAT ATGTATAAAT TAATACAGAG TACGTAAAA GCAAAAAGAT GTATATTTGC       3341

ATATTTTTCT AAAGAAATAT ATTATTCATC TTTTCATTCA AAAAAAAAAA AAAAGAGCTC      3401

AATTCCCGGG GATCC                                                      3416
```

( 2 ) INFORMATION FOR SEQ ID NO:25:

( i ) SEQUENCE CHARACTERISTICS:
        ( A ) LENGTH: 180 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Arg Phe Thr Phe Thr Ser Arg Cys Leu Ala Leu Phe Leu Leu Leu
 1           5                  10                 15

Asn His Pro Thr Pro Ile Leu Pro Ala Phe Ser Asn Gln Thr Tyr Pro
            20                 25                 30

Thr Ile Glu Pro Lys Pro Phe Leu Tyr Val Val Gly Arg Lys Lys Met
        35                 40                 45

Met Asp Ala Gln Tyr Lys Cys Tyr Asp Arg Met Gln Gln Leu Pro Ala
    50                 55                 60

Tyr Gln Gly Glu Gly Pro Tyr Cys Asn Arg Thr Trp Asp Gly Trp Leu
65                 70                 75                 80

Cys Trp Asp Asp Thr Pro Ala Gly Val Leu Ser Tyr Gln Phe Cys Pro
            85                 90                 95

Asp Tyr Phe Pro Asp Phe Asp Pro Ser Glu Lys Val Thr Lys Tyr Cys
            100                105                110

Asp Glu Lys Gly Val Trp Phe Lys His Pro Glu Asn Asn Arg Thr Trp
        115                120                125

Ser Asn Tyr Thr Met Cys Asn Ala Phe Thr Pro Glu Lys Leu Lys Asn
    130                135                140

Ala Tyr Val Leu Tyr Tyr Leu Ala Ile Val Gly His Ser Leu Ser Ile
145                150                155                160

Phe Thr Leu Val Ile Ser Leu Gly Ile Phe Val Phe Phe Ser Ser His
            165                170                175

Val Tyr His Glu
        180
```

( 2 ) INFORMATION FOR SEQ ID NO:26:

( i ) SEQUENCE CHARACTERISTICS:
        ( A ) LENGTH: 3390 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: plsex ( i x ) FEATURE:
        ( A ) NAME/KEY: CDS
        ( B ) LOCATION: 52..1485

( x i ) SEQUENCE DESCRIPTION: SEQ ID NO:26:

```
GAATTCGCGG CCGCCAGAAT TCCAGGACAA AGAGATCTTC AAAAATCAAA A ATG AGG       57
```

|   |   |   |   |   |   |   |   |   |   |   |   |   |   | Met<br>1 | Arg |  |
|---|---|---|---|---|---|---|---|---|---|---|---|---|---|---|---|---|
| TTC | ACA | TTT | ACA | AGC | CGG | TGC | TTG | GCA | CTG | TTT | CTT | CTT | CTA | AAT | CAC | 105 |
| Phe | Thr<br>5 | Phe | Thr | Ser | Arg | Cys | Leu<br>10 | Ala | Leu | Phe | Leu | Leu<br>15 | Leu | Asn | His |  |
| CCA | ACC | CCA | ATT | CTT | CCT | GCC | TTT | TCA | AAT | CAA | ACC | TAT | CCA | ACA | ATA | 153 |
| Pro | Thr<br>20 | Pro | Ile | Leu | Pro | Ala<br>25 | Phe | Ser | Asn | Gln | Thr<br>30 | Tyr | Pro | Thr | Ile |  |
| GAG | CCC | AAG | CCA | TTT | CTT | TAC | GTC | GTA | GGA | CGA | AAG | AAG | ATG | ATG | GAT | 201 |
| Glu<br>35 | Pro | Lys | Pro | Phe | Leu<br>40 | Tyr | Val | Val | Gly | Arg<br>45 | Lys | Lys | Met | Met | Asp<br>50 |  |
| GCA | CAG | TAC | AAA | TGC | TAT | GAC | CGA | ATG | CAG | CAG | TTA | CCC | GCA | TAC | CAA | 249 |
| Ala | Gln | Tyr | Lys | Cys<br>55 | Tyr | Asp | Arg | Met | Gln<br>60 | Gln | Leu | Pro | Ala | Tyr<br>65 | Gln |  |
| GGA | GAA | GGT | CCA | TAT | TGC | AAT | CGC | ACC | TGG | GAT | GGA | TGG | CTG | TGC | TGG | 297 |
| Gly | Glu | Gly | Pro<br>70 | Tyr | Cys | Asn | Arg | Thr<br>75 | Trp | Asp | Gly | Trp | Leu<br>80 | Cys | Trp |  |
| GAT | GAC | ACA | CCG | GCT | GGA | GTA | TTG | TCC | TAT | CAG | TTC | TGC | CCA | GAT | TAT | 345 |
| Asp | Asp | Thr<br>85 | Pro | Ala | Gly | Val | Leu<br>90 | Ser | Tyr | Gln | Phe | Cys<br>95 | Pro | Asp | Tyr |  |
| TTT | CCG | GAT | TTT | GAT | CCA | TCA | GAA | AAG | GTT | ACA | AAA | TAC | TGT | GAT | GAA | 393 |
| Phe | Pro<br>100 | Asp | Phe | Asp | Pro | Ser<br>105 | Glu | Lys | Val | Thr | Lys<br>110 | Tyr | Cys | Asp | Glu |  |
| AAA | GGT | GTT | TGG | TTT | AAA | CAT | CCT | GAA | AAC | AAT | CGA | ACC | TGG | TCC | AAC | 441 |
| Lys<br>115 | Gly | Val | Trp | Phe | Lys<br>120 | His | Pro | Glu | Asn | Asn<br>125 | Arg | Thr | Trp | Ser | Asn<br>130 |  |
| TAT | ACT | ATG | TGC | AAT | GCT | TTC | ACT | CCT | GAG | AAA | CTG | AAG | AAT | GCA | TAT | 489 |
| Tyr | Thr | Met | Cys | Asn<br>135 | Ala | Phe | Thr | Pro | Glu<br>140 | Lys | Leu | Lys | Asn | Ala<br>145 | Tyr |  |
| GTT | CTG | TAC | TAT | TTG | GCT | ATT | GTG | GGT | CAT | TCT | TTG | TCA | ATT | TTC | ACC | 537 |
| Val | Leu | Tyr<br>150 | Tyr | Leu | Ala | Ile | Val | Gly<br>155 | His | Ser | Leu | Ser | Ile<br>160 | Phe | Thr |  |
| CTA | GTG | ATT | TCC | CTG | GGG | ATT | TTC | GTG | TTT | TTC | AGG | AAG | GCA | TTG | AGC | 585 |
| Leu | Val | Ile<br>165 | Ser | Leu | Gly | Ile | Phe<br>170 | Val | Phe | Phe | Arg | Lys<br>175 | Ala | Leu | Ser |  |
| CTT | GGC | TGC | CAA | AGG | GTA | ACC | CTG | CAC | AAG | AAC | ATG | TTT | CTT | ACT | TAC | 633 |
| Leu | Gly<br>180 | Cys | Gln | Arg | Val | Thr<br>185 | Leu | His | Lys | Asn | Met<br>190 | Phe | Leu | Thr | Tyr |  |
| ATT | CTG | AAT | TCT | ATG | ATT | ATC | ATC | ATC | CAC | CTG | GTT | GAA | GTA | GTA | CCC | 681 |
| Ile | Leu<br>195 | Asn | Ser | Met | Ile<br>200 | Ile | Ile | Ile | His | Leu<br>205 | Val | Glu | Val | Val | Pro<br>210 |  |
| AAT | GGA | GAG | CTC | GTG | CGA | AGG | GAC | CCG | GTG | AGC | TGC | AAG | ATT | TTG | CAT | 729 |
| Asn | Gly | Glu | Leu | Val<br>215 | Arg | Arg | Asp | Pro | Val<br>220 | Ser | Cys | Lys | Ile | Leu<br>225 | His |  |
| TTT | TTC | CAC | CAG | TAC | ATG | ATG | GCC | TGC | AAC | TAT | TTC | TGG | ATG | CTC | TGT | 777 |
| Phe | Phe | His | Gln<br>230 | Tyr | Met | Met | Ala | Cys<br>235 | Asn | Tyr | Phe | Trp | Met<br>240 | Leu | Cys |  |
| GAA | GGG | ATC | TAT | CTT | CAT | ACA | CTC | ATT | GTC | GTG | GCT | GTG | TTT | ACT | GAG | 825 |
| Glu | Gly | Ile | Tyr<br>245 | Leu | His | Thr | Leu | Ile<br>250 | Val | Val | Ala | Val | Phe<br>255 | Thr | Glu |  |
| AAG | CAA | CGC | TTG | CGG | TGG | TAT | TAT | CTC | TTG | GGC | TGG | GGG | TTC | CCG | CTG | 873 |
| Lys | Gln | Arg<br>260 | Leu | Arg | Trp | Tyr | Tyr<br>265 | Leu | Leu | Gly | Trp | Gly<br>270 | Phe | Pro | Leu |  |
| GTG | CCA | ACC | ACT | ATC | CAT | GCT | ATT | ACC | AGG | GCC | GTG | TAC | TTC | AAT | GAC | 921 |
| Val | Pro | Thr | Thr<br>275 | Ile | His | Ala | Ile | Thr<br>280 | Arg | Ala | Val | Tyr<br>285 | Phe | Asn | Asp<br>290 |  |
| AAC | TGC | TGG | CTG | AGT | GTG | GAA | ACC | CAT | TTG | CTT | TAC | ATA | ATC | CAT | GGA | 969 |
| Asn | Cys | Trp | Leu | Ser<br>295 | Val | Glu | Thr | His<br>300 | Leu | Leu | Tyr | Ile | Ile<br>305 | His | Gly |  |
| CCT | GTC | ATG | GCG | GCA | CTT | GTG | GTC | AAT | TTC | TTC | TTT | TTG | CTC | AAC | ATT | 1017 |

```
Pro Val Met Ala Ala Leu Val Val Asn Phe Phe Phe Leu Leu Asn Ile
            310                 315                 320

GTC CGG GTG CTT GTG ACC AAA ATG AGG GAA ACC CAT GAG GCG GAA TCC   1065
Val Arg Val Leu Val Thr Lys Met Arg Glu Thr His Glu Ala Glu Ser
        325                 330                 335

CAC ATG TAC CTG AAG GCT GTG AAG GCC ACC ATG ATC CTT GTG CCC CTG   1113
His Met Tyr Leu Lys Ala Val Lys Ala Thr Met Ile Leu Val Pro Leu
        340                 345                 350

CTG GGA ATC CAG TTT GTC GTC TTT CCC TGG AGA CCT TCC AAC AAG ATG   1161
Leu Gly Ile Gln Phe Val Val Phe Pro Trp Arg Pro Ser Asn Lys Met
355                 360                 365                 370

CTT GGG AAG ATA TAT GAT TAC GTG ATG CAC TCT CTG ATT CAT TTC CAG   1209
Leu Gly Lys Ile Tyr Asp Tyr Val Met His Ser Leu Ile His Phe Gln
                375                 380                 385

GGC TTC TTT GTT GCG ACC ATC TAC TGC TTC TGC AAC AAT GAG GTC CAA   1257
Gly Phe Phe Val Ala Thr Ile Tyr Cys Phe Cys Asn Asn Glu Val Gln
            390                 395                 400

ACC ACC GTG AAG CGC CAA TGG GCC CAA TTC AAA ATT CAG TGG AAC CAG   1305
Thr Thr Val Lys Arg Gln Trp Ala Gln Phe Lys Ile Gln Trp Asn Gln
            405                 410                 415

CGT TGG GGG AGG CGC CCC TCC AAC CGC TCT GCT CGC GCT GCA GCC GCT   1353
Arg Trp Gly Arg Arg Pro Ser Asn Arg Ser Ala Arg Ala Ala Ala Ala
        420                 425                 430

GCT GCG GAG GCT GGC GAC ATC CCA ATT TAC ATC TGC CAT CAG GAG CTG   1401
Ala Ala Glu Ala Gly Asp Ile Pro Ile Tyr Ile Cys His Gln Glu Leu
435                 440                 445                 450

AGG AAT GAA CCA GCC AAC AAC CAA GGC GAG GAG AGT GCT GAG ATC ATC   1449
Arg Asn Glu Pro Ala Asn Asn Gln Gly Glu Glu Ser Ala Glu Ile Ile
                455                 460                 465

CCT TTG AAT ATC ATA GAG CAA GAG TCA TCT GCT TGAATGTGAA GGCAAACACA   1502
Pro Leu Asn Ile Ile Glu Gln Glu Ser Ser Ala
                470                 475

GCATCGTGAT CACTGAGCCA TCATTTCCTG GAGAAAGAC CATGCATTTA AAGTATTCTC   1562
CATCCTCCCA GGAACCGAAC ATATCATTTG TGAAGAATTA TTCAGTGAAT TTGTCCATTG   1622
TAAATCTGAA GAAAGTTATT CTTGGTACTG TTGCTTTGGG AGACAGTCTA GGAATGGAGT   1682
CTCCCACTGC AACTTGTGAA CTCCATCATT CATCCAGGAC TGAGATGCAA ATGTCACAGT   1742
AATGCAAGCA AAGTATCAAA GAAAAACAAT GAAATTGACC TAGTTCAGAT ACAGGGTGCT   1802
CCTTGTCAAT ACTGAGCCAT TTATACCTTT GAAATATTAA AATCACTGTC AATATTTTTA   1862
TTTTTAACTC TGGATTTTGA ATTAGATTAT TTCTGTATTT GGCTATGGAT CTGATTTTTA   1922
ATTTTTTTAA ATTTCAGTCA ATTCTGATGT TACTGAGATG TTTTACCATC CTTACAATGT   1982
AAACCACATG AACTACGTGA CCTCTGCAAG ACAAAGCGGC TTTCTAATAG AGAGATTAGT   2042
AAATATGTGA AGAAAAAGAC CTGCATTTGG CAGGAAGATG TATGCTTTGA ATGCAAAAGA   2102
AATTTAGAGT CAATTTGCTG AAAACATTAC ATGCTCAGCT TGGTTTTGGA CAAGCCTGTC   2162
CATTGGGCAG GACCTAGCTG TTGTAAAGAA TTGGTCTTAA TGTTGAATGT ATTTTGGTTG   2222
CTGATGTTTA TAAACTGAGA GGTCACAAAG AATCTATCAC TAAAAATTTT TACAAAACTG   2282
CCAAAAATAT AATTCTTAGT GGAAGACAAT ACTCCCTTTA AAGAGAGTTT GCCACTCCCC   2342
TAAACTCCAG GATTTATAAA GCAAATTACT CCAAGGTTTA TAAAGCAGAT TACCTCTTGC   2402
CCTTGGGTGC TATCTAGCAG TAAAAGATAA ATTTGTTGAA TATTGGTAAT TAAAAGACTC   2462
CACATAAGTC CATTAACTGC TTTCCACCCA GCTTCAAAGC TTAAAAAGAG CTCAGGCTTT   2522
TCCAGGAAGA TCCAGGAGGG CTAATTAGAA ATCAACTTGT GGTTGACCGC TTGTTTCTTG   2582
TTATTACCAA ACAGGAGGGG AAAAAATTAA CTGCTCCAAA TTTAACCATA AATCAATTCA   2642
```

```
TGTTTAACGT TTCTCATTAA AATCCAGTAT TATATTATCA TATCTCTCTT TACTTCCCAG    2702
TATAAGATTT TTGAAAATCC TGAATAAACC AGTATCGTTA CTGGCACCTG AAATTAATTT    2762
GTGAATTTGC AACAGTAATC AGAGTTACCA TTATTTAATT TGTATGCTAA ATGAGGAGGT    2822
ACATTGAAAC CCTCCAAATC TCCAGTCTCA TCTATGTCAT ATTTTGCCAC TGCCTTTCAG    2882
AAGTGATTTA GTTGTGGAAA GATAATAAAT TGATTTGTTA TGGTTACATA TTTAGCGCAC    2942
CCAGAGAAAA TTAATTATAT TTCTACAGAG AAAATGAATT TGGGATACTA AAGTAGTTTA    3002
AGTCTCCTTT ACTGAATGTA AGGGGGGGAT CGAAAAGAAG GTATTTTCC AATCACAGTG    3062
TTATGTAGTA TTGTTCTATT TTTGTTTACA AACATGGAAA ACAGAGTATT TCTGGCAGCT    3122
GTGGTACAAA TGTGATAATA TATTGCTAAA ATATTTAGA TGTTATTATG CTAATATAGT    3182
AGGGGTTGAA GAAAACAAAA TAGCTTATTA TAGAATTGCA CATAGTTCTG CCCAAATTAT    3242
GTGAAATGCT TATGCTTGTG TATATGTATA AATTAATACA GAGTACGTTA AAAGCAAAAA    3302
GATGTATATT TGCATATTTT TCTAAAGAAA TATATTATTC ATCTTTTCAT TCAAAAAAAA    3362
AAAAAAGAG CTCAATTCCC GGGGATCC                                        3390
```

( 2 ) INFORMATION FOR SEQ ID NO:27:

( i ) SEQUENCE CHARACTERISTICS:
        ( A ) LENGTH: 477 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Arg Phe Thr Phe Thr Ser Arg Cys Leu Ala Leu Phe Leu Leu Leu
 1               5                  10                  15

Asn His Pro Thr Pro Ile Leu Pro Ala Phe Ser Asn Gln Thr Tyr Pro
                20                  25                  30

Thr Ile Glu Pro Lys Pro Phe Leu Tyr Val Val Gly Arg Lys Lys Met
            35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
                100                 105                 110

Asp Glu Lys Gly Val Trp Phe Lys His Pro Glu Asn Asn Arg Thr Trp
            115                 120                 125

Ser Asn Tyr Thr Met Cys Asn Ala Phe Thr Pro Glu Lys Leu Lys Asn
130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Lys Ala
                165                 170                 175

Leu Ser Leu Gly Cys Gln Arg Val Thr Leu His Lys Asn Met Phe Leu
                180                 185                 190

Thr Tyr Ile Leu Asn Ser Met Ile Ile Ile Ile His Leu Val Glu Val
            195                 200                 205

Val Pro Asn Gly Glu Leu Val Arg Arg Asp Pro Val Ser Cys Lys Ile
210                 215                 220
```

```
Leu His Phe Phe His Gln Tyr Met Met Ala Cys Asn Tyr Phe Trp Met
225             230                 235                 240

Leu Cys Glu Gly Ile Tyr Leu His Thr Leu Ile Val Val Ala Val Phe
                245                 250                 255

Thr Glu Lys Gln Arg Leu Arg Trp Tyr Tyr Leu Leu Gly Trp Gly Phe
            260                 265                 270

Pro Leu Val Pro Thr Thr Ile His Ala Ile Thr Arg Ala Val Tyr Phe
        275                 280                 285

Asn Asp Asn Cys Trp Leu Ser Val Glu Thr His Leu Leu Tyr Ile Ile
    290                 295                 300

His Gly Pro Val Met Ala Ala Leu Val Val Asn Phe Phe Phe Leu Leu
305                 310                 315                 320

Asn Ile Val Arg Val Leu Val Thr Lys Met Arg Glu Thr His His Glu Ala
                325                 330                 335

Glu Ser His Met Tyr Leu Lys Ala Val Lys Ala Thr Met Ile Leu Val
            340                 345                 350

Pro Leu Leu Gly Ile Gln Phe Val Val Phe Pro Trp Arg Pro Ser Asn
        355                 360                 365

Lys Met Leu Gly Lys Ile Tyr Asp Tyr Val Met His Ser Leu Ile His
    370                 375                 380

Phe Gln Gly Phe Phe Val Ala Thr Ile Tyr Cys Phe Cys Asn Asn Glu
385                 390                 395                 400

Val Gln Thr Thr Val Lys Arg Gln Trp Ala Gln Phe Lys Ile Gln Trp
            405                 410                 415

Asn Gln Arg Trp Gly Arg Arg Pro Ser Asn Arg Ser Ala Arg Ala Ala
            420                 425                 430

Ala Ala Ala Ala Glu Ala Gly Asp Ile Pro Ile Tyr Ile Cys His Gln
        435                 440                 445

Glu Leu Arg Asn Glu Pro Ala Asn Asn Gln Gly Glu Glu Ser Ala Glu
    450                 455                 460

Ile Ile Pro Leu Asn Ile Ile Glu Gln Glu Ser Ser Ala
465                 470                 475
```